Figure 1B:
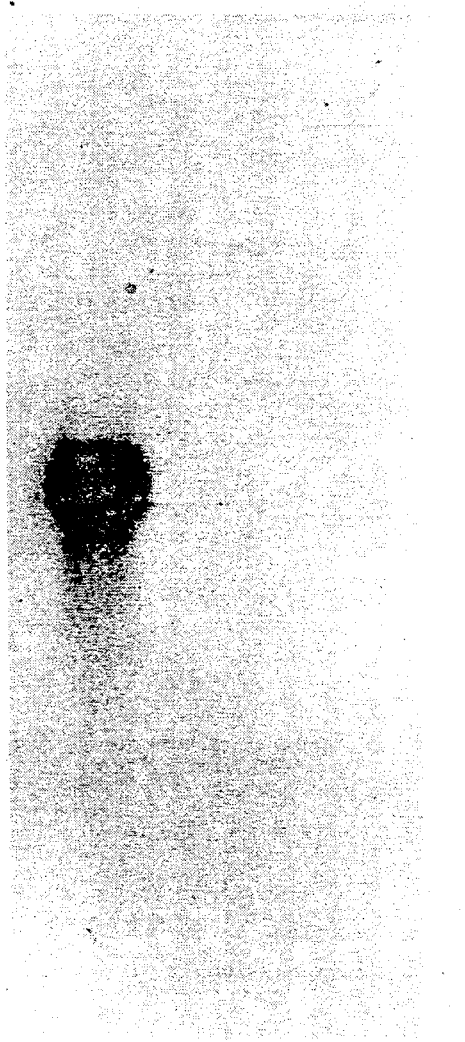

United States Patent [19]

Cantor et al.

[11] Patent Number: 5,238,839

[45] Date of Patent: Aug. 24, 1993

[54] NUCLEIC ACIDS ENCODING PROTEINS WHICH INDUCE IMMUNOLOGICAL EFFECTOR CELL ACTIVATION AND CHEMATTRACTION, VECTORS, AND RECOMBINANT CELLS

[75] Inventors: Harvey I. Cantor, Wellesley; Roberto Patarca, Brookline; Joel L. Schwartz, Newton Centre; Gordon J. Freeman, Brookline, all of Mass.

[73] Assignee: Dana Farber Cancer Institute, Boston, Mass.

[21] Appl. No.: 732,185

[22] Filed: Jul. 18, 1991

Related U.S. Application Data

[62] Division of Ser. No. 153,887, Feb. 9, 1988, Pat. No. 5,049,659.

[51] Int. Cl.$^5$ .................... C12N 5/10; C12N 1/21; C12N 15/19
[52] U.S. Cl. .................... 435/240.1; 435/320.1; 435/240.2; 435/252.3; 435/252.33; 435/254.2; 536/23.5
[58] Field of Search ............. 435/320.1, 252.33, 256, 435/240.1, 240.2, 240.2, 252.3, 255; 536/27, 23.5

[56] References Cited

U.S. PATENT DOCUMENTS 4,792,525  12/1988  Ruoslahti et al. .

OTHER PUBLICATIONS

Oldberg et al. Proc. Natl. Acad. Sci. USA, vol. 83, pp. 8819–8823 Dec. 1986.
David et al., Proc. Natl. Acad. Sci. U.S.A. 56:72–77 (1966).
Ward et al., Fed. Proc. 30:1721–1724 (1971).
Altman et al., J. Immunol 110:801–810 (1973).
North, J. Immunol. 121:806–809 (1978).
Cameron et al., J. Clin. Invest 63:977–984 (1979).
Montovani et al., Int. J. Cancer 25:691–699 (1980).
Steeg et al., J. Exp. Med. 152:1734 (1980).
De Weck et al., Biochemical Characterization of Lymphokines, Academic Press, New York (1980).
Rocklin et al., Adv. Immunol. 29:56–136 (1980).
Nabel et al., Cell 23:19–28 (1981).
Fresno et al., Cell 30:707–713 (1982).
Campbell et al., Immunol. Today 7:70–72 (1986).
Clark and Kamen, Science 236:1229–1237 (1987).
Pace et al., J. Immunol. 130:2011–2013 (1983).
Schultz et al., Nature (Lond.) 305:239–240 (1983).
Svedersky et al., J. Exp. Med. 159:812–827 (1984).
Celada et al., J. Exp. Med. 160:55–74 (1984).
Ward et al., Science 163:1079–1081 (1969).
Ward et al., Cell. Immunol. 1:162–174 (1970).
Boraschi and Tagliabue Eur. J. Immunol 11:110–134 (1981).
Andrew et al., Euro. J. Immunol. 14:962–964 (1984).
Kleinerman et al., Cancer Res. 44:4470–4475 (1984).
Lee et al., J. Immunol 136(4):1322–1328 (1986).
Fidalgo and Najjar, Biochemistry 6:3386–3392 (1967).
Najjar and Nishioka, Nature 228:672–673 (1970).
Najjar Adv. Enzymol. 41:129–178 (1974).
Fridkin et al., Biochem. Biophys. Acta 496:203–211 (1977).

(List continued on next page.)

*Primary Examiner*—Nina Ossanna
*Attorney, Agent, or Firm*—Pennie & Edmonds

[57] ABSTRACT

The present invention relates to genes and their encoded proteins which induce immunological effector cell activation and chemattraction. The proteins of the invention attract subsets of immunological effector cells and stimulate them to express their specialized effector cell functions. Such proteins, termed Ap-1 proteins, are expressed by lymphoid cells, and bind to effector cells such as macrophages and mast cells. In particular, the Ap-1 proteins induce macrophage phagocytosis, expression of class II major histocompatibility molecules, cytotoxicity, and migration, and induce hematopoietic progenitor cell differentiation. The Ap-1 molecules can be of value in the therapy or diagnosis of inflammatory or immune disorders, or neoplasia.

25 Claims, 24 Drawing Sheets

OTHER PUBLICATIONS

Ward, Amer. J. Pathol. 54:121–128 (1969).
Ward and Newman, J. Immunol. 102:93–99 (1969).
Bevilacqua et al., J. Exp. Med. 153:42–60 (1981).
Wright and Meyer, J. Exp. Med. 162:762–767 (1985).
Ruoslahti and Pierschbacher, Cell 44:517–518 (1986).
Campbell et al., J. Clin. Invest. 75:2085–2090 (1985).
Franzen and Heinegard, Biochem. J. 232:715–724 (1985a).
Franzen and Heinegard, in Chemistry and Biology of Mineralized Tissues, Botler, W. T., ed., EBSCO, pp. 132–141 (1985b).
Bohmann et al., Science 238:1386–1392 (1987).
Lee et al., Cell 49:741–752 (1987).
Angel et al., Nature 332:166–171 (1988).
Halazonetis et al., Cell 55:917–24 (1988).
Franza et al., Biological Abstract 85:abstract no. 121339 (1988).
Waschek et al., Chemcial Abstract 100:abstract no. 89725a (1989).
Spandidos et al., Chemcial Abstract 110:abstract No. 70279m (1989).
New England Biolabs Catalog, 1986/87.
Maniatis et al., 1982 Molecular Cloning: A laboratory manual. Cold Sping Harbor laboratory, Cold Spring Harbor, N.Y.
Campaell et al, Nature 329:744–46 (1987).
Miyazaki et al., Nucl. Acids Res. 17:3290 (1989).
Craig et al., Biochem. Biophys. Res. Comm. 157:166–173 (1988).
Smith et al., J. Cell. Biochem. 34:13–22 (1987).
Craig et al., J. Biol. Chem. 264:9682–9689 (1989).

FIG. 1A a b c d e f g h i j

Kb

- 6

- 1.765
- 1.426

- 0.92

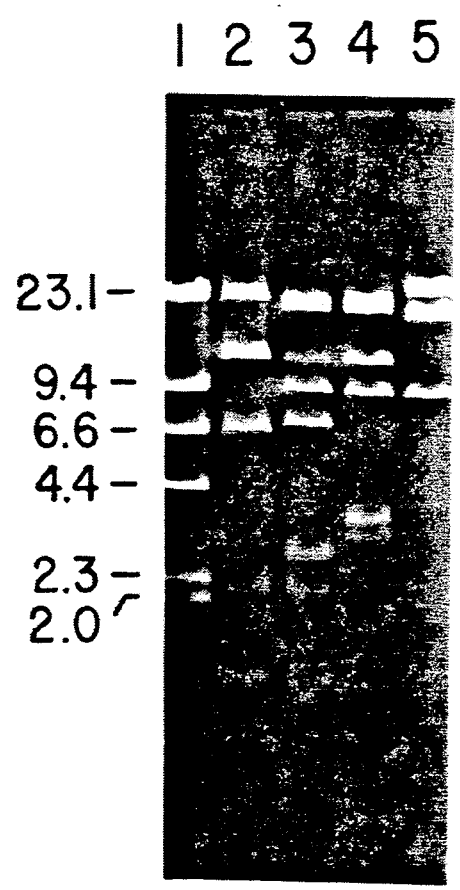

FIG. 2B

```
  1  GGGGGGGGGGGGGGGGGGCTTTCTTGCTCTTATGAGAGGTGGAGAGGTAGAAAAGGCACACAAATATTGACT
 81  CACTGAAATTTCTCTGAGATGTAGAAAGATTCCATAAAATTATTGGTGACTTGGTGTGATCTAGTGGTGCCAAGAGTGT
161  GTTTGAACCTGACAAGACATTCAACTGTGCCCTCATAAAAATATGTTGCAGGACTAACTACGACCATGAGATTGGCAGTGATT
                                                                  M  R  L  A  V  I      6

241  TGCTTTGCCTGTGTTGGCATTGCCTCCTCCCGGTGAAAGTGACTGATTCTGGCAGCTCAGAGGAGAAGCTTTACAG
      C  F  C  L  F  G  I  A  S  S  L  P  V  K  V  T  D  S  G  S  S  E  E  K  L  Y  S    33

321  CCTGCACCCAGATCCTATAGCCACATGGCCGTGCCTGACCCATCCAGAAGCAGAATCTCCTTGCCCACAGAATGCTG
      L  H  P  D  P  I  A  T  W  P  V  P  D  P  S  Q  K  Q  N  L  L  A  P  Q  N  A  V    60

401  TGTCCTCTGAAGAAAAGGATGACTTTAAGCAAGAAACTCTTCCAAGCAATTCCAATGAAAGCCACCATGGACGAC
      S  S  E  E  K  D  D  F  K  Q  E  T  L  P  S  N  S  N  E  S  H  D  H  M  D  D      113

481  GATGATGACGATGATGACGATGAGACCATGCAGAGAGCGAGGATTCTGTGACTCGGATGAATCTGACCAATCTCA
      D  D  D  D  D  D  D  D  G  D  H  A  E  S  E  D  S  V  D  S  D  E  S  H              140

561  CCATTCGATGAGTCTGATGAGACCCTCAGTAGTACACAAGCAGACACTTTCACTCCAATCGTCCCTACAGTCGATG
      H  S  D  E  S  D  E  T  V  T  A  S  T  Q  A  D  T  F  T  P  I  V  P  T  V  D  V    166

641  TCCCCAACGGCCGAGGTGATAGCTTGGCTTATGGACTGAGGTCAAAGTCTAGGAGTTTCCAGTTTCTGATGAACAGTAT
      P  N  G [R  G  D] S  L  A  Y  G  L  R  S  K  S  R  S  F  Q  V  S  D  E  Q  Y
```

FIG. 2B (cont.)

```
721   CCTGATGCCACAGATGAGGACCTCACCCTCTCACATGAAGAGCGGTGAGTCTAAGGACTCCCTCGATGTCATCCCTGTGC
      P  D  A  T  D  E  D  L  T  L  S  H  M  K  S  G  E  S  K  E  S  L  D  V  I  P  V  A    193

801   CCAGCTTCTGAGCATGCCCTCTGATCAGGACAACAACGGAAAGGGCAGCCATGAGTCAAGTCAGTTGGATGAACCAAGTC
      Q  L  L  S  M  P  S  D  Q  D  N  N  G  K  G  S  H  E  S  S  Q  L  D  E  P  S  L    220

881   TGGAAACACAGACTTGAGCATTCCAAAGAGAGCCAGGAGTGCCGATCAGTCGATGTGATAGTCAAGCAAGT
      E  T  H  R  L  E  H  S  K  E  S  Q  E  S  A  D  Q  S  D  V  I  D  S  Q  A  S       246

961   TCCAAAGCCAGCTGGAACATCAGAGCCACAAGTTTCACAGCCACAAGGACAAGCTAGTCCTAGACCCTAAGAGTAAGGA
      S  K  A  S  L  E  H  Q  S  H  K  F  H  S  H  K  D  K  L  V  L  D  P  K  S  K  E    273

1041  AGATGATAGGTATCTGAAATTCCGAATTCTCATGAATTAGAGAGTTCATCTTCTGAGGTCAACTAAAGAAGAGGCAAAA
      D  D  R  Y  L  K  F  R  I  S  H  E  L  E  S  S  S  S  E  V  N  *                   294

1121  ACACAGTTCCTTACTTTGCATTTAGTAAAAACAAGAAAAAGTGTTACTGAGGGTTAAGCAGGAATACTAACTGCTCATTT
1201  CTCAGTTCAGTTGGATATATGTATGTAGAGAAAAGAGAGGTAATATTTTGGCCTCTTAGCTTAGTCTCTGTTCTTTCATGCAAA
1281  CACCGTTGTAACCAAAGCTTCTGCACTTGCTCGTGTACAAGAAATGCAACGGCCACTGCATTTAATGA
1361  TTGTTATTCTTTCATGAATAAAATGTATGTAGAATAAGTAAGTTACTGAGAATTACTGAAACAAGCAAGAATTAAAAGAGAAACTGTA
1441  ACAGTCTATATCACTATACCTTTTAGTTTTATAATTAGCATATATTTTATTTTTTTGTGTGTGAA
1521  TAAATCTTGTTAACGAAAAAAAAAAAAAAAAAAAAAA
```

FIG. 3B

| Pos | Sequence | Pos | Protein |
|---|---|---|---|
| 300 | CTC AGA GAA AAG CTT TAC | 26 | SSEEK |
| 405 | CTC TGA AGA AAA GGA TGA C | 61 | SSEEK |
| 538 | TCG GAT GAA TCT GAC GAA GAC | 106 | SDESDES |
| 565 | TCG GAT GAG TCT GAT GAG AC | 115 | SDESDET |
| 768 | TCT AAG GAG TCC CTG GA | 182 | SKESLD |
| 904 | TTC CAA AGA GAG CCA GGA | 227 | SKES Q |
| 960 | TTC CAA AGC CAG CCT GGA | 246 | SK A SLE |
| 981 | TCA G AGC CAC AAG | 254 | SHK |
| 996 | TCA C AGC CAC AAG | 258 | SHK |

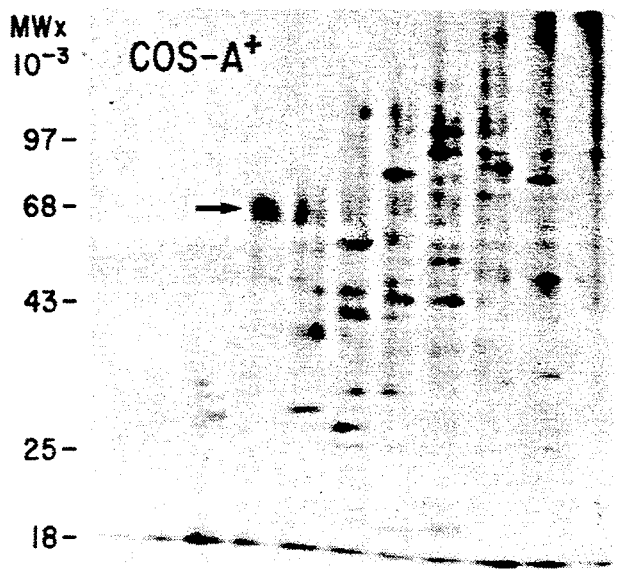
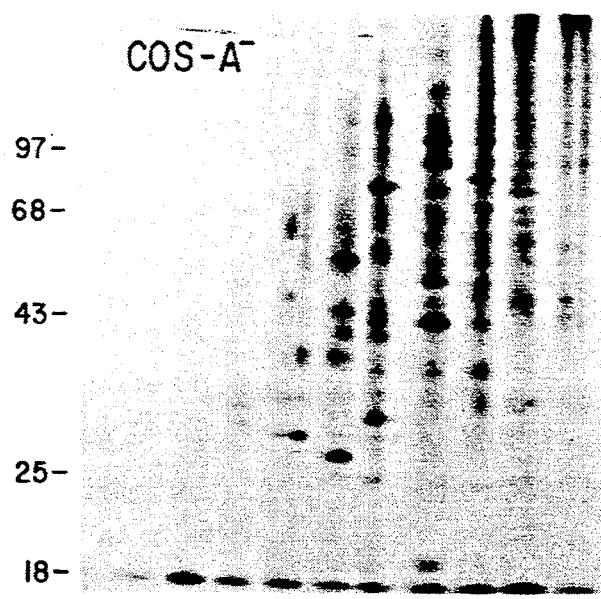
FIG. 4C

FIG. 8C. COS-A⁻ 24HRS 100X
FIG. 8D. COS-A⁺+RGD OCTAMER 24HRS 100X
FIG. 8A. COS-A⁺ 24HRS 100X
FIG. 8B. COS-A⁺: 24HRS 200X

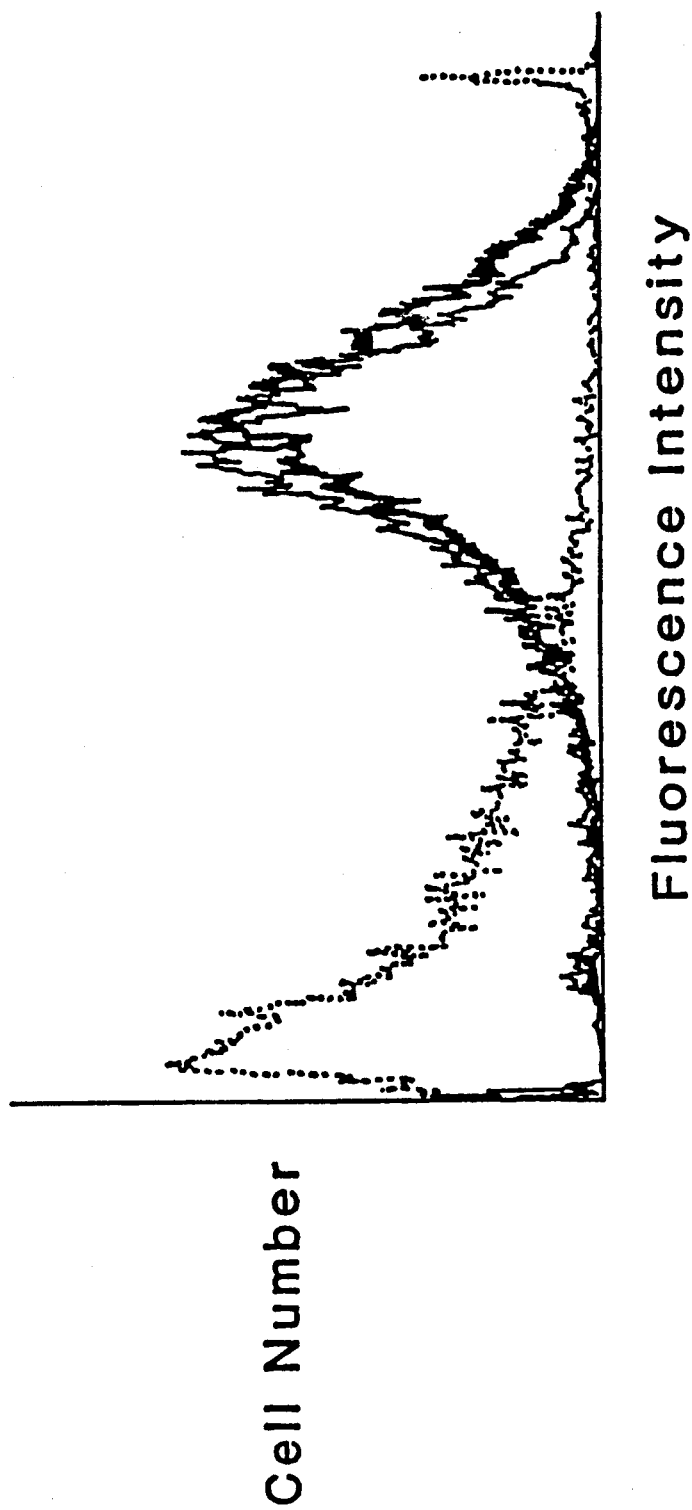

NUCLEIC ACIDS ENCODING PROTEINS WHICH INDUCE IMMUNOLOGICAL EFFECTOR CELL ACTIVATION AND CHEMATTRACTION, VECTORS, AND RECOMBINANT CELLS

Pursuant to the provisions of 35 U.S.C. §202(c), it is hereby acknowledged that the Government has certain rights in this invention, which was made in part with funds from the National Institutes of Health.

This is a division of application Ser. No. 07/153,887, filed Feb. 9, 1988, which issued on Sep. 17, 1991 as U.S. Pat. No. 5,049,659.

TABLE OF CONTENTS

Figure 5:
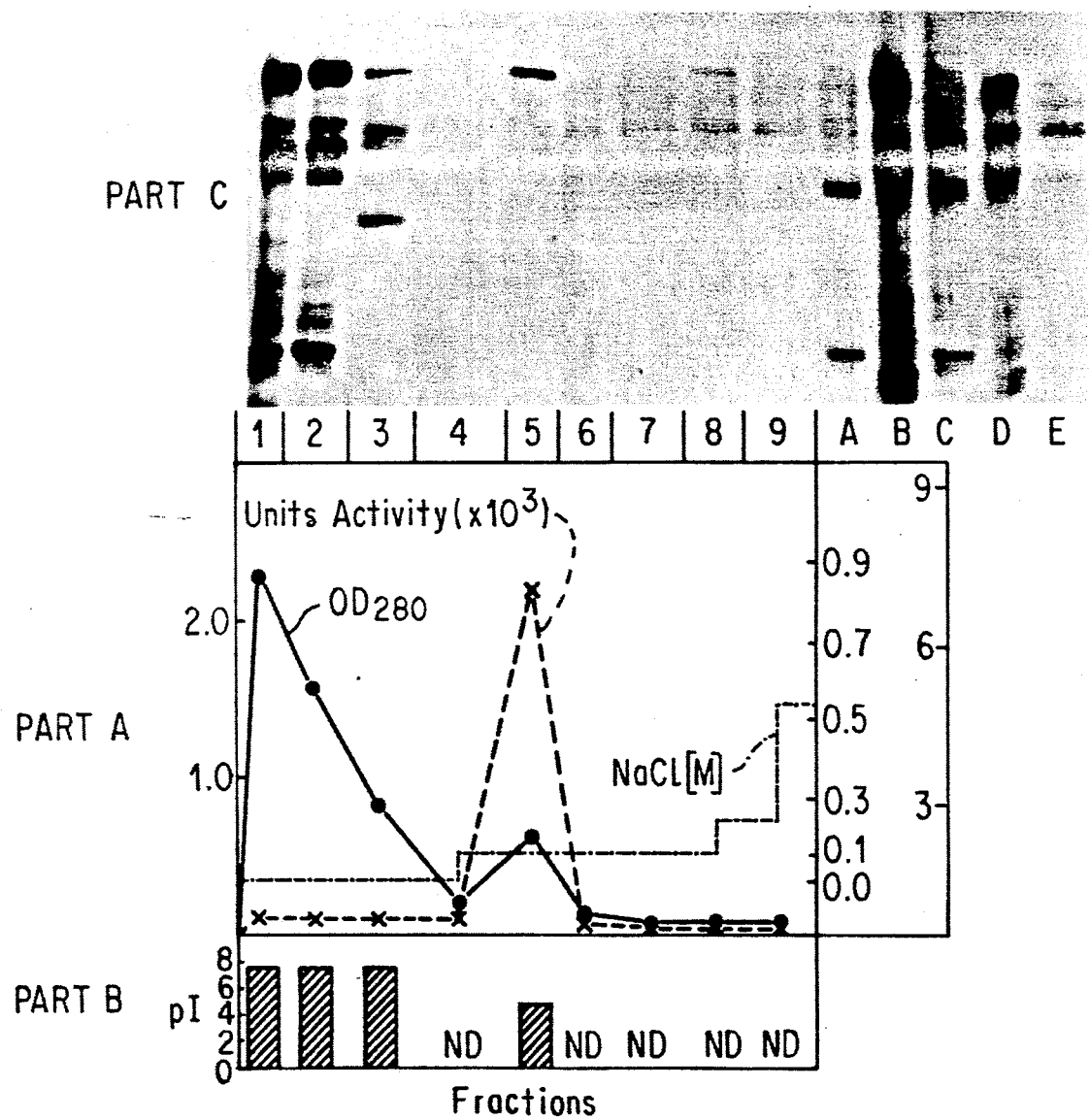

1. Introduction
2. Background of the Invention
3. Summary of the Invention
   3.1 Definitions
4. Description of the Figures
5. Detailed Description of the Invention
   5.1. Isolation of the Ap-1 Gene
   5.2. Expression of the Cloned Ap-1 Gene
   5.3. Identification and Purification of the Expressed Gene Product
   5.4. Structure of the Ap-1 Gene and Protein
      5.4.1. Genetic Analysis
      5.4.2. Protein Analysis
   5.5. Properties of Ap-1
      5.5.1. Immunological Effector Cell Binding
      5.5.2. Immunological Effector Cell Activation
      5.5.3. Immunological Effector Cell Chemattraction
      5.5.4. Induction of Immunological Effector Cell Cytotoxicity
      5.5.5 Induction of Granulocyte/Monocyte Progenitor Cell Differentiation
   5.5. Anti-Ap-1 Antibody Production
   5.7. Ap-1-Related Derivatives, Analogues, and Peptides
   5.8. Uses of Ap-1
      5.8.1. Modulation of the Immunological Effector Cell Response
      5.8.2. Assays
         5.8.2.1. Immunoassays
         5.8.2.2. Hybridization Assays
6. Isolation and Characterization of an Ap-1 Protein Produced by T Lymphocytes
   6.1. Experimental Procedures
      6.1.1 T Cell Clones
      6.1.2. Activation of T Cell Clones for cDNA Library Preparation
      6.1.3. RNA Isolation
      6.1.4. cDNA Synthesis
      6.1.5. cDNA Hybridizations
         6.1.5.1. Preparation of a Probe Specific for T Lymphocyte Genes
         6.1.5.2. Southern Blotting
      6.1.6. cDNA Library Preparation
      6.1.7. Colony Hybridization
      6.1.8. Nucleotide Sequence Determination
      6.1.9. Transfections and Labelling of Cells
      6.1.10. Northern Blotting
      6.1.11. Slot Blot Analysis for Expression of Ap-1 RNA
      6.1.12. Analysis of Recombinant Ap-1
      6.1.13. Two Dimensional Gel Electrophoresis
      6.1.14. Synthetic Peptides and Purified Proteins
      6.1.15. Production of Antibodies
      6.1.16. Mast Cells
      6.1.17. Macrophage Content in Peritoneal Cells
      6.1.18. Binding of Labelled Ap-1 to Cells
      6.1.19. Expression of Ia by Macrophages
         6.1.19.1. Assay by Indirect Immunofluorescence
         6.1.19.2. FACS Analysis of Ia Expression by Macrophages
      6.1.20. Indirect Immunofluorescent Detection of Ap-1
      6.1.21. Macrophage Chemotaxis Assays
         6.1.21.1. Dish Assay
         6.1.21.2. Modified Boyden Chamber Asssay
      6.1.22. Assay of Macrophage Tumoricidal Activity
      6.1.23. Induction of Granulocyte/Monocyte Colonies
      6.1.24. Screening of a Human Genomic Library with the Murine Ap-1 cDNA Probe
   6.2. Isolation of a cDNA Encoding Ap-1
   6.3. Isolation of Human Genomic Ap-1 Clones
   6.4. Structure of Ap-1
   6.5. Expression of Ap-1 in COS Cells
   6.6. Purification of Ap-1
   6.7. Analysis of Biologically Active Subsequences of Ap-1
      6.7.1. Ap-1 Binding to Subsets of Immunological Cells
      6.7.2. Contribution of the RGD-Containing Subsequence to Ap-1 Attachment
   6.8. Analysis of Biological Activities of Ap-1
      6.8.1. Macrophage Chemotactic Activity
      6.8.2. Macrophage Activation: Ia Induction
         6.8.2.1. Assay by Indirect Immunofluorescence
         6.8.2.2. FACS Analysis
      6.8.3. Macrophage Activation: Phagocytosis
      6.8.4. Macrophage Activation: Induction of Cytotoxicity
      6.8.5. Induction of Granulocyte/Monocyte Progenitor Cell Differentiation
   6.9. Expression of Ap-1 in Autoimmune Mice
   6.10. Discussion of the Biological Activities of Ap-1
7. Deposit of Microorganisms

1. INTRODUCTION

The present invention relates to genes and their encoded proteins that induce immunological effector cell activation and chemattraction. The proteins of the invention attract subsets of immunological effector cells and stimulate them to express their specialized effector cell functions. Such proteins, termed Ap-1 proteins, are expressed by lymphoid cells, and bind to effector cells such as macrophages and mast cells. In particular, the Ap-1 proteins induce macrophage phagocytosis, expression of class II major histocompatibility molecules, cytotoxicity, and migration, and induce hematopoietic progenitor cell differentiation. The Ap-1 molecules can be therapeutically valuable in the treatment or prevention of inflammatory or immune disorders, or neoplasia.

2. BACKGROUND OF THE INVENTION

A critical component of an inflammatory response initiated by activated lymphocytes is attraction of macrophages and other immunological effector cells to the site of the reaction.

When a lymphocyte recognizes a foreign antigen, e.g., on the surface of cells infected with a virus or bacterium, the lymphocyte is not equipped to destroy microbial agents rapidly and efficiently. Elimination of pathogens and infected cells depends upon attraction and activation of immunological effector cells such as macrophages and neutrophils (Metchnikoff, E., 1893, Lectures on the Comparative Pathology of Inflammation, Kegan Paul, London; reviewed by Campbell, P., 1986, Immunol. Today 7:70–72). Activated T cells secrete a panel of peptides that induce other subsets of immunological cells to express their respective functions (Nabel, G., et al., 1981, Cell 23:19-28; Fresno, M., et al., 1982, Cell 30:707-713). Definition of the genes that encode these peptides has depended on sensitive and reproducible assays that measure the biological activity of a particular peptide. This approach has identified several biologically active proteins produced by T cells (e.g., IL-2, IL-3, IL-4 and gamma-interferon).

The factors which stimulated T lymphocytes produce that induce various changes in macrophage function and physiology, including increases in effector cell functions (North, R. J., 1978, J. Immunol. 121:806; Rocklin, R. E., et al., 1980, Adv. Immunol. 29:56), have been termed macrophage-activating factors (MAF). Such MAF include gamma-interferon (Pace, J. L., et al., 1983, J. Immunol. 130:2011; Schultz, R. M. and Kleinschmidt, W. J., 1983, Nature (Lond.) 305:239; Svedersky, L. P., et al., 1984, J. Exp. Med. 159:812; Celada, A., et al., 1984, J. Exp. Med. 160:55–74). Activation of macrophage tumoricidal activity by gamma-interferon usually requires a second signal provided by endotoxin or lipopolysaccharide. In contrast, analysis of MAF activity in supernatant fluids of T cells indicates that tumoricidal activity may be mediated by material which does not require the presence of endogenous or added endotoxin, and may be serologically distinguishable from gamma-interferon (Boraschi, D., and Tagliabue, A., 1981, Eur. J. Immunol. 11:110-134; Andrew, P. W., et al., 1984, Eur. J. Immunol. 14:962; Kleinerman, E. S., et al., 1984, Cancer Res. 44:4470-4475; Lee, J., et al, 1986, J. Immunol. 136(4):1322-1328).

Evidence that activated lymphocytes produced soluble factors that might induce (Altman, L. C., et al., 1973, J. Immunol. 110:801) or inhibit (David, J. R., 1966, Proc. Natl. Acad. Sci. U.S.A. 56:72-77) macrophage migration has stimulated an extensive effort to define molecules responsible for these activities (Cameron, D. J. and Churchill, W. H., 1979, J. Clin. Invest. 63:977-984; Mantovani A. et al. 1980, Int J. Cancer 25:691-699; Steeg, P. S., et al., 1980, J. Exp. Med. 152:1734; for a review, see DeWeck, A. L., et al., eds., 1980, Biochemical Characterization of Lymphokines, Academic Press, New York). Tuftsin is a tetrapeptide (TKPR) that is the active fragment of leukophilic gamma-globulin, which stimulates migration and phagocytosis of macrophages and polymorphonuclear granulocytes (Najjar, V. A., 1974, Adv. Enzymol. 41:129-178; Najjar, V. A. and Nishioka, K., 1970, Nature 228:672; Fidalgo, B. V. and Najjar, V. A., 1967, Biochim. Biophys. Acta 496:203-211). Complement-derived factors have been shown to be chemotactic for mononuclear cells (Ward, P. A. and Newman, L. J., 1969, J. Immunol. 102:93), for eosinophils, and for neutrophils (Ward, P. A., 1969, Amer. J. Pathol. 54:121).

The RGD tripeptide marks a family of molecules that may induce changes in cellular motility and/or differentiation in a variety of cell types (reviewed by Ruoslahti, E. and Pierschbacher, M. D., 1986, Cell 44:517-518). The most well-studied member of this family is fibronectin, which has an RGD-containing subsequence similar to that present in Ap-1 (id.). Fibronectin, in conjunction with collagen or gelatin, can attach to macrophages, promoting an increase in surface receptors for immunoglobulin and for the C3b component of the complement proteins (Bevilacqua, M. P., et al., 1981, J. Exp. Med. 162:762-767).

There may be several instances of cell-cell interactions mediated by RGD-DGR complementarity. Studies of the association between MHC class I antigens and viruses have shown that Semliki Forest virus closely associates with a class I molecule in lipid bilayers (Helenius, A., et al., 1978, Proc. Natl. Acad. Sci. U.S.A. 75:3846-3850). Class I MHC molecules from different species contain a highly conserved DGR sequence. The glycophorin C molecule, which displays a DGR subsequence (Colin, Y., et al., 1986, J. Biol. Chem. 261:229–233), has been associated with penetration of Plasmodium merozoites into red blood cells and interaction with viruses and extracellular membrane (Pasvol, G., et al., 1984, Lancet 1:907-908).

Osteopontin (Oldberg, A., et al., 1986, Proc. Natl. Acad Sci. U.S.A. 83:8819-8823; Franzen A. and Heinegard, D., 1985, Biochem. J. 232:715-724; Franzen, A. and Heinegard, D., 1985, in Chemistry and Biology of Mineralized Tissues, Botler, W. T., ed., EBSCO, pp. 132-141) is a bone sialoprotein that contains an RGD cell-binding sequence, and is highly homologous to Ap-1. No immunological effector cell activity for osteopontin has been shown, and osteopontin is reported to be present solely in bone (id.). Osteopontin contains two additional repeats of a subsequence that is present only once in Ap-1, and contains a pentapeptide, YKQRA, absent from Ap-1. Furthermore, there are a total of 43 encoded amino acid residues which differ between Ap-1 and osteopontin, out of which 28 are nonconservative substitutions.

The extracellular matrix of bone marrow has been shown to contain an adhesive protein, termed haemonectin, of approximately 60,000 molecular weight and isoelectric point of about 4.5, which promotes selective attachment of cells of the granulocyte lineage (Campbell, A. D., et al., 1987, Nature 329:744-746). Haemonectin was not detectable in matrix preparations from spleen, mammary gland, or kidney (id.).

3. SUMMARY OF THE INVENTION

The present invention relates to genes, and their encoded proteins which induce activation and mediate chemattraction of immunological effector cells. The proteins of the invention, termed Ap-1 (activation protein-1), bind specifically to effector cells such as macrophages and mast cells, and induce immunological effector cell cytotoxicity toward target cells. The proteins of the invention induce macrophage phagocytosis, expression of class II major histocompatibility complex (MHC) molecules on the cell surface, and migration, and participate in the inflammatory response. In addition, the Ap-1 proteins stimulate hematopoietic progenitor cell differentiation.

Ap-1, and analogues, derivatives, or subsequences thereof, or antibodies to epitopes thereof, can have valuable uses in diagnostics and therapy of immune and inflammatory disorders, and neoplasia.

In a particular embodiment of the present invention detailed in the examples sections infra, a murine Ap-1 protein of approximately 60,000 molecular weight and an isoelectric point of about 4.5 is described. Two representative Ap-1 genes, a murine Ap-1 cDNA clone and a human genomic Ap-1 clone, are also described. The murine Ap-1 gene is shown to be expressed at elevated levels in mice with an autoimmune disorder.

3.1. DEFINITIONS

As used herein, the following abbreviations will have the meanings indicated:
Ap-1 = activation protein-1
Ap-1(FxD) = purified Ap-1, as represented by fraction D of the DEAE-cellulose ion exchange chromatographic fractions described in Section 6.6, infra
BSA = bovine serum albumin
cDNA = complementary DNA
ConA = concanavalin A
COS-A+ supernatant = supernatant from COS cells transfected with the Ap-1 cDNA clone pCD-Ap-1
COS-A-supernant = supernatant from COS cells transfected with the parental pCD vector (containing no Ap-1-specific sequences)
FACS = fluorescent activated cell sorter
FCS = fetal calf serum
FITC = fluorescein isothiocyanate
FMLP = N-formyl methionylphenylalanine
G/M CSF = granulocyte/monocyte colony stimulating factor
IEF = isoelectric focusing
IF = interferon
IL = interleukin
kb = kilobase pair
kd = kilodalton
LPS = lipopolysaccharide
MAF = macrophage activating factor
NK = natural killer cell(s)
ORF = open reading frame
PAGE = polyacrylamide gel electrophoresis
PBL = peripheral blood lymphocytes
PBS = phosphate-buffered saline
PHA = phytohemagglutinin
pI = isoelectric point
RPM = resident peritoneal macrophages
SDS = sodium dodecyl sulfate
TCA = trichloroacetic acid
$T_H$ = T helper cell(s)

4 DESCRIPTION OF THE FIGURES

FIG. 1A. Northern analysis of Ap-1 expression. A $^{32}$P-labelled, nick-translated 1.7 kb XhoI fragment, containing the Ap-1 cDNA insert from the pCD vector, was hybridized to filters containing 5 ug of poly(A)+ RNA isolated from the following cells:
a. Cl.Lyl-N5 (TH clone)
b. Cl.Lyl-N5 + concanavalin A (ConA)
c. Cl.Lyl-Sl ($T_H$ clone)
d. Cl.Lyl-Sl + ConA
e. NK-11 (Thy1+ NK clone)
f. NK-11 + Con A
g. MC.9 (mast cell clone)
h. MC.9 + ConA
i. 2PK3 (B cell line)
j. human peripheral blood lymphocytes (PBL) + phytohemagglutinin (PHA)
and exposed for autoradiography. RNA markers are indicate on the right, corresponding to 6, 1.765, 1.426, and 0.92 kb.

FIG. 1B Northern blot (over-exposed) of 5 ug of poly(A)+RNA from:
a. Cl.Lyl.Tl ($T_H$ clone) + ConA
b. thymocytes
c. spleen cells
hybridized to a $^{32}$P-labelled, nick translated 1.7 kb XhoI fragment, containing the Ap-1 cDNA insert from the pCD vector, and exposed for autoradiography.

FIG. 1C. Ethidium bromide staining pattern of DNA of a human genomic Ap-1 clone. A human genomic library was screened with an Ap-1 cDNA probe as described in Section 6.1.25. DNA from positive plaques was isolated and digested with the appropriate restriction enzyme before agarose gel electrophoresis and ethidium bromide staining. Lane 1: DNA molecular weight standards; lane 2: human genomic isolate Hi92, digested with BamHI and EcoRI; lane 3: Hi92, digested with SalI and EcoRI; lane 4: Hi92, digested with SalI and BamHI; lane 5: Hi92, digested with SalI. Southern hybridization data for the fragments of isolate Hi92 shown in FIG. 1C is presented in FIG. 1D.

Figure 1A:
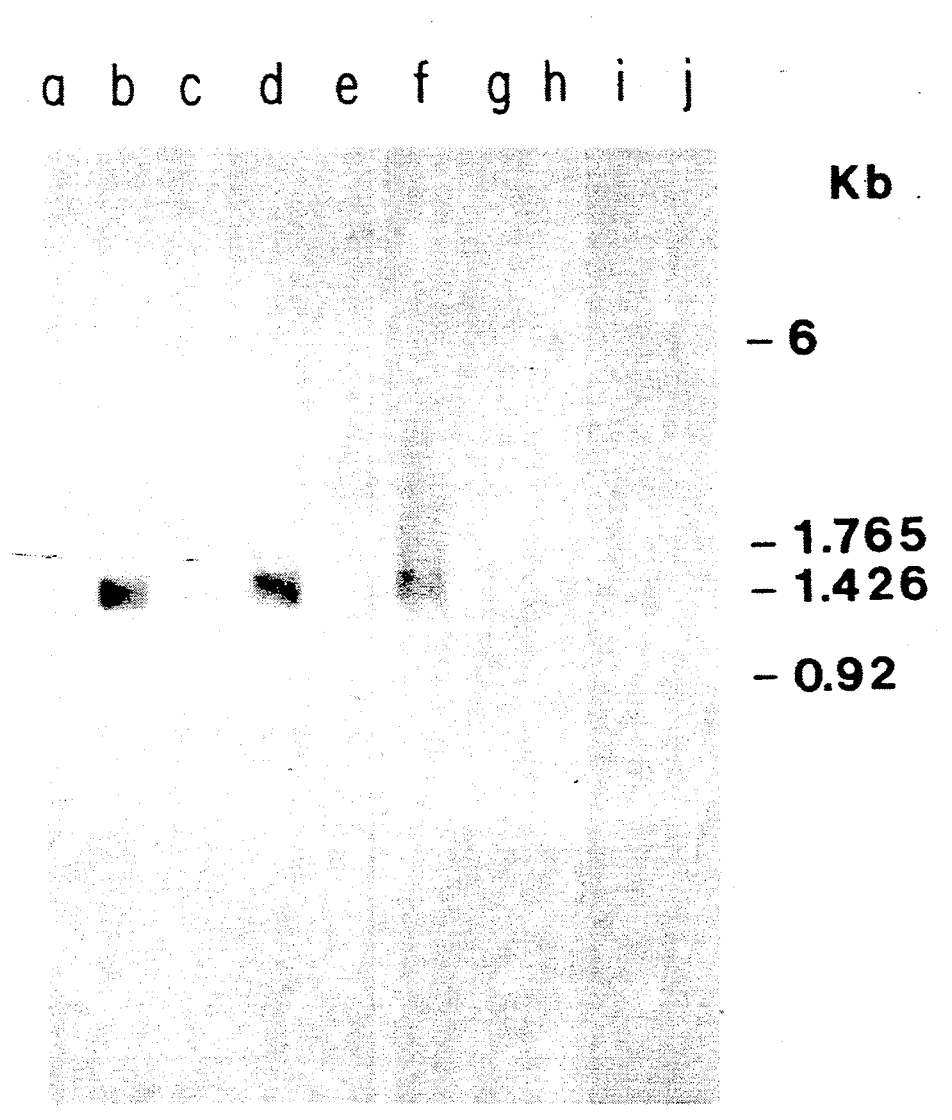
Figure 1D:
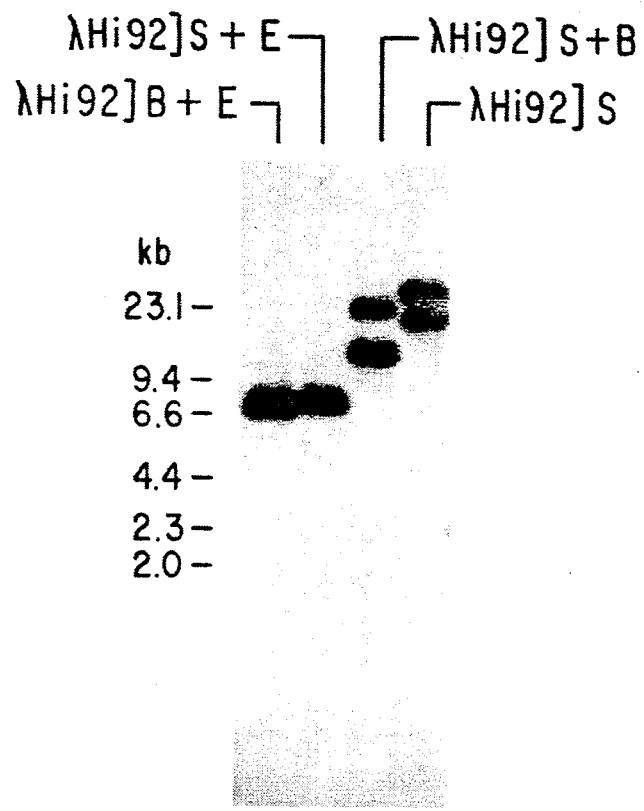

FIG. 1D. Southern analysis of human genomic clone Hi92. Hybridization of human genomic isolate Hi92 to the Ap-1 cDNA probe (XhoI fragment) is shown. The Hi92 insert was digested with: Lane 1, BamHI+EcoRI; Lane 2, SalI+EcoRI; Lane 3, SalI+BamHI; Lane 4, SalI.

Figure 2A:
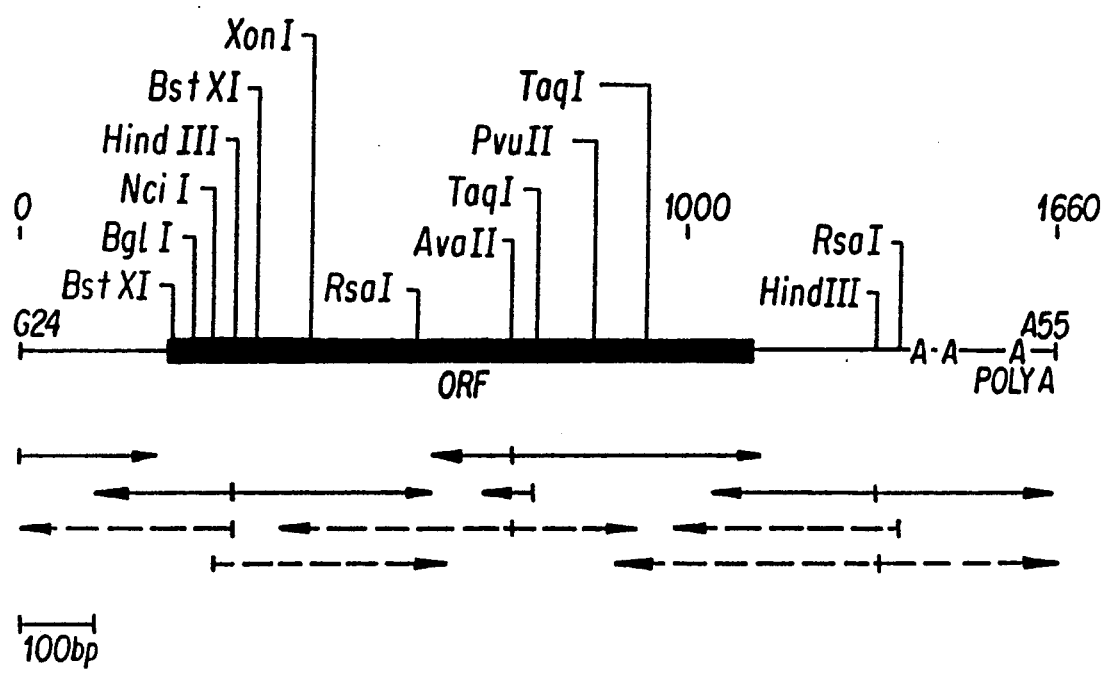

FIG. 2A. Restriction endonuclease cleavage map of the cDNA insert of Ap-1. The coding region (open reading frame, ORF) is shaded in black. The sequencing strategy used is shown below the map, with the arrows indicating the direction and approximate extent of nucleotide sequence obtained. The $^{32}$P-labeled 5' end of the DNA fragment used for sequencing is at the base of the arrows. A: potential polyadenylation site.

FIG. 2B. Nucleotide and predicted amino acid sequence of Ap-1. The sequenced cDNA of 1569 bp is shown. An open reading frame of 882 nucleotides (294 amino acids) is followed by a 3'-noncoding sequence that contains three potential polyadenylation sites shown in lower case letters.

Figure 3A:
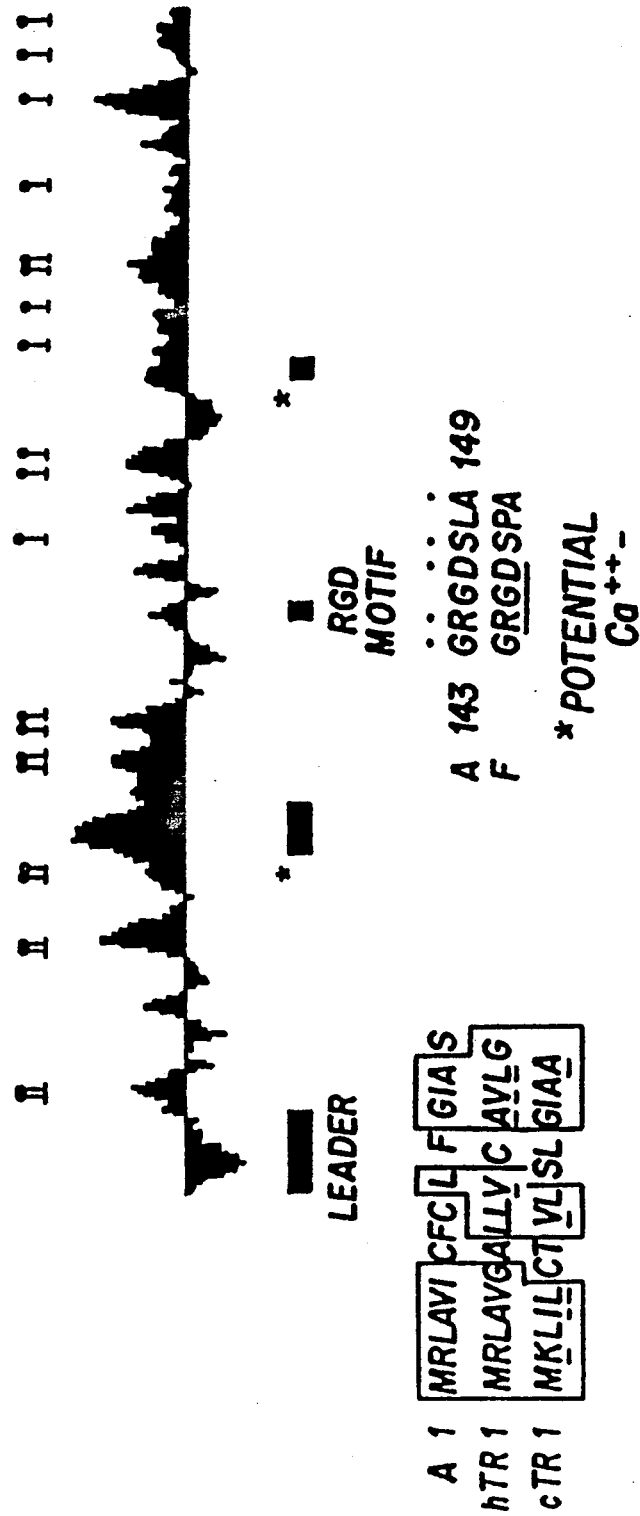

FIG. 3A. Hydrophilicity plot of the Ap-1 protein. A hydrophilicity plot for the deduced amino acid sequence of Ap-1 was obtained using the algorithm of Hopp and Woods (1981, Proc. Natl. Acad. Sci. U.S.A. 78:3824). Hydrophilic regions are shown above the main line; hydrophobic regions are shown below. The location of various subsequences are indicated. Potential glycosylation sites are indicated by closed and open circles. The leader sequences of murine Ap-1 (A), human transferrin (hTF), and chicken transferrin (cTF) are shown at left. Two potential $Ca^{++}$ binding sites in Ap-1 (amino acid residues 85 to 94 and 200 to 207) are compared with potential $Ca^{++}$ binding sites from thrombospondin (T) (amino acids 718 to 727, and 769 to 776). The RGD-containing subsequence (amino acids 143 to 149) is compared to that of fibronectin (F).

FIG. 3B. Repeat sequences at the nucleotide and protein sequence levels in Ap-1. Left panel: Nucleotide repeats from the sequence shown in FIG. 2B are compared, for the regions consisting of the following nucleotides: 300-318 vs. 405-423; 538-557 vs. 565-584; 768-784 vs. 904-921 vs. 960-977; 981-993 vs. 996-1008. Right panel: Comparison of four amino acid repeats from the sequence shown in FIG. 2B.

FIG. 4. Part A: Northern analysis of COS cells transfected with pCD-Ap-1 or (parental) pCD. 72 hours after transfection of COS cells with pCD-Ap-1 (lane a) or with pCD (lane b), Ap-1 transcription was assayed for by hybridization of 5 ug of poly(A)+ RNA to the nick-translated XhoI fragment of the Ap-1 cDNA as probe (shown in FIG. 2A). Hybridization revealed a 2.2 kb RNA produced in pCD-Ap-1-transfected cells (lane a), which corresponds to the expected size of the Ap-1 cDNA insert (1.55 kb) plus SV40 sequence (0.5 kb) plus poly(A) (0.15 kb). Part B: Northern analysis at various time points of COS cells transfected with pCD-Ap-1 or pCD. The XhoI fragment of the Ap-1 cDNA clone was used as probe for the indicated amounts of total COS cell RNA isolated at various times after transfection:

a. 72 a. 72 hours after transfection with pCD-Ap-1,
b. pCD vector without cDNA insert at 72 hours,
c. pCD vector without cDNA insert at 80 hours,
d. 80 hours after transfection with pCD-Ap-1, and
e. 96 hours after transfection with pCD-Ap-1.

FIG. 4C. Two dimensional isoelectric focusing/electrophoretic analysis of supernatant fluids from transfected COS cells. Upper panel: Electrophoretic analysis of COS-A+ supernatant. $^{35}$S-methionine-labelled supernatants of COS cells transfected with pCD-Ap-1 was subjected to two dimensional gel separation as described in Section 6.1.13, and exposed for autoradiography. The arrow indicates a 60 kd protein band, from supernatants of COS cells transfected with the pCD-Ap-1 vector, which is absent from supernatants of COS cells transfected with the parental pCD vector (lower panel). The numbers at left indicate the positions of migration of molecular weight protein standards.

FIG. 5A. Analysis of proteins in COS-A+ supernatant fluids. COS-A+ supernatant supplemented with 0.1% BSA (1 ug/ml) was analyzed by DEAE-chromatography as described in Section 6.1.12 and 6.6. The absorbance (280 nm) of pooled fractions (— —) eluted at the indicated concentrations of NaCl (—.—.—) is compared with units of macrophage activating factor (MAF) activity (—X—) contained in each pooled fraction. DEAE chromatography of COS-A− supernatant did not reveal detectable protein, as measured by absorbance (280 nm), in fractions eluted with 0.1M to 1 M NaCl buffer.

FIG. 5B. Analysis of proteins in COS-A+ supernatant fluids. The panel below shows the mean pI (isoelectric point) obtained after electrophoresis of 15 ul of each fraction on an isoelectric focusing gel calibrated with myoglobulin, bovine serum albumin, phycocyanin, and carbonic anhydrase. Fraction 5 contained a single protein species according to densitometric tracing, with an apparent pI of 4.5.

FIG. 5C. Analysis of proteins in COS-A+ supernatant fluids. The upper panel depicts the proteins revealed by silver staining after electrophoresis of 10 microliters of each DE-52 (DEAE ion-exchange) fraction in 10% SDS-polyacrylamide gel electrophoresis, for fractions 1-9. Lanes A, C, and D represent migration of molecular weight standards bovine serum albumin, ovalbumin, and carbonic anhydrase. Lane B shows the analysis of COS-A+ supernatant fluids. Lane A shows background staining, of the ion-exchange buffer.

Figure 6A:
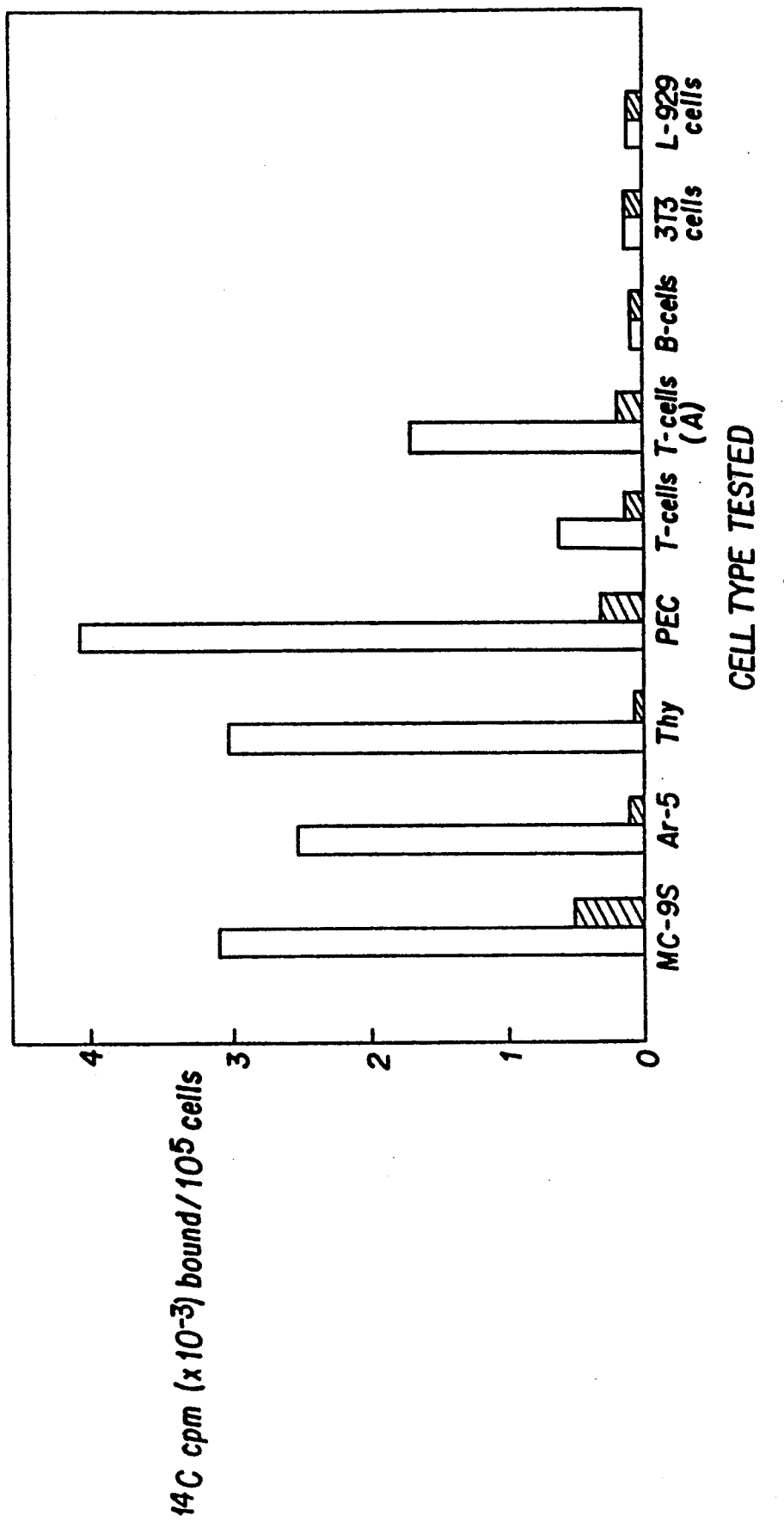

FIG. 6A. Binding of Ap-1 to different cell types. $10^5$ cells were incubated for 15 minutes in 0.1 ml medium containing $5 \times 10^2$ to $6 \times 10^4$ cpm of $^{14}$C-COS-A+ (transfected with pCD-Ap-1) supernatant or $^{14}$C-COS-A− (transfected with parental pCD) supernatant, at room temperature. The results shown represent the cpm bound at saturation of binding, i.e., after addition of $1.5 \times 10^4$ cpm to $10^5$ cells from MC/tlC9 (mast cell clone), Ar-5 (T$_H$ clone), Thy (thymocytes), PEC (adherent fraction of peritoneal cells), T cells (spleen cells after passage through nylon wool columns), T-cells A [nylon wool-passed spleen cells obtained 24 hours after incubation with ConA (2 ug/ml)], B cells (Ig+ fraction of spleen cells), NIH3T3 (3T3) cells, or L-929 cells. In addition to the data shown, cold COS-A+ supernatant was added to $^{14}$C-labeled COS-A+ supernatant (containing $10^4$ cpm), at a final concentration of 50:1 (cold:labeled) Ap-1 (with the Ap-1 concentration determined by immunoprecipitation of COS cell supernatant with the IgG fraction of a rabbit antibody raised against a hydrophilic portion of Ap-1). Cpm bound by the first six cell types indicated in the graph were reduced to less than 500 cpm in each case.

Figure 6B:
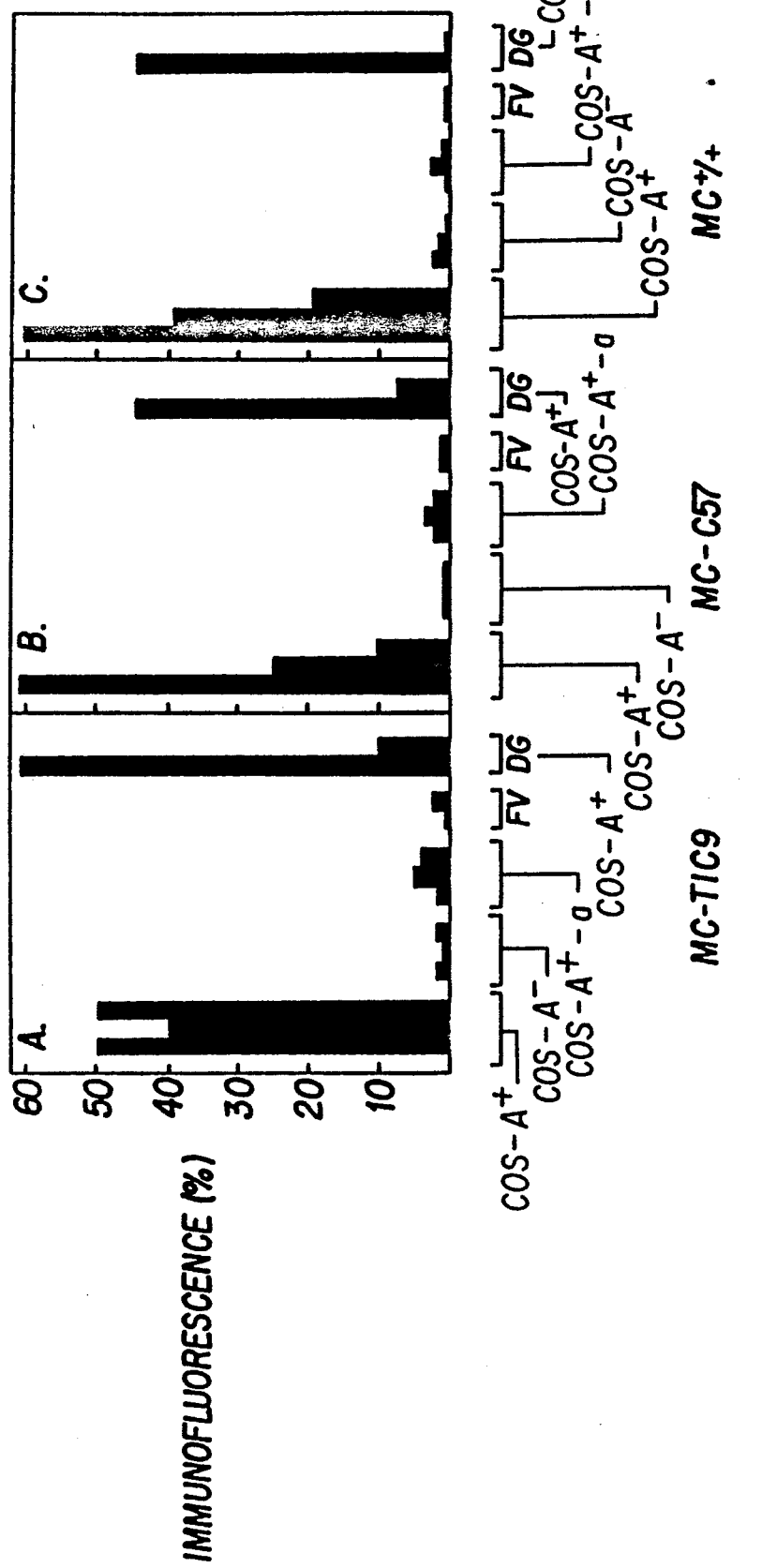

FIG. 6B. Ap-1 binding to mast cells.

COS-A+, COS-A−: $10^6$ cells from a growth factor-dependent, uncloned mast cell population (Panel C) (WBB6F$_1$-+/+ mast cells) and from two growth factor-independent cloned mast cell lines (Cl.MC/tlC9,Panel A; Cl.MC/C57.1, Panel B) were incubated with 0.5 ml, 0.1 ml, and 0.01 ml of COS-A+ supernatant. The IgG fraction of a rabbit antiserum ("R anti-RGD") raised against a hydrophilic subsequence of the Ap-1 molecule, was added, at a 1:100 serum dilution, at 4° C. After 20 minutes, the cells were washed twice and fluorescein-conjugated goat anti-rabbit IgG (1:50 dilution in PBS as supplied) was added. After 20 minutes, the cells were washed 3 times, fixed with paraformaldehyde +2% FCS for 2 minutes, and washed 5 times with DMEM (Dulbecco's Minimal Essential Medium). Percentage fluorescence was determined by observation of 25 random fields under 100× magnification on each of three coverslips/dish. A total of 500 cells/coverslip were counted.

COS-A+a: COS-A+ a refers to immunofluorescence of mast cells after incubation with COS-A+ supernatant that had been preincubated with the rabbit anti-RGD antiserum followed by precipitation in 50% (NH Values for COS-A+ supernatant incubated with normal rabbit IgG did not differ significantly from those obtained with COS-A+ supernatant.

F;V: Cells were incubated with 100 ug/ml of fibronectin (F) or vitronectin (V) before indirect immunofluorescence was performed as above, using rabbit anti-fibronectin or rabbit anti-vitronectin antibody.

COS-A++DG: Cells were incubated with 0.1 ml COS-A+ supernatant (containing approximately 0.1 to 1 ug of Ap-1, as determined by immunoprecipitation of COS-A+ supernatant) and 500 ug of the synthetic octapeptide D (DDDDDDDD) or octapeptide G (NGRGDSLA), before immunofluorescent analysis.

Figure 7:
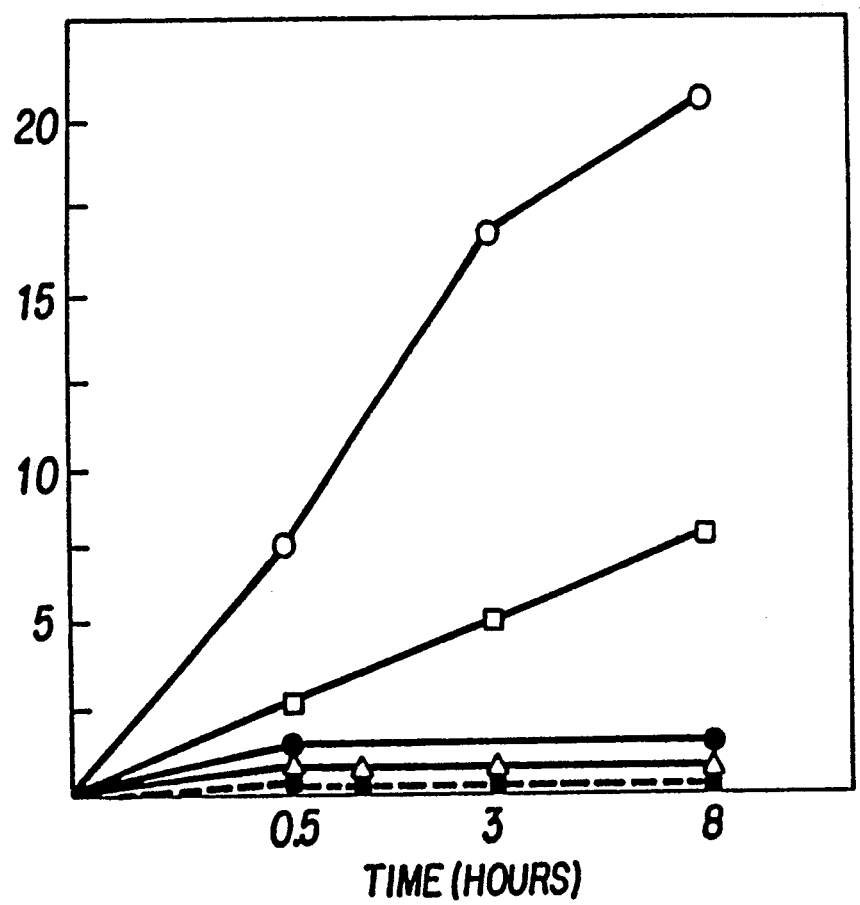

FIG. 7. Macrophage migration in a gradient of recombinant Ap-1. Adherent cells ($4 \times 10^5$) from the peritoneal cavity of C57/B6 mice (greater than 98% peroxidase positive) were placed at four equidistant points at the circumference of a 60 mm dish containing a central 15 mm well of sepharose 4B beads saturated with the materials indicated below. At intervals after the beads were placed in the well, the numbers of cells located 0-5 mm, 5-15 mm, and 15-20 mm from the circumference were quantified. At the intervals indicated on the abscissa, the mean distance from the origin of 50% of the cells was determined in dishes containing beads saturated with: COS-A+ supernatant (0.5 ml) (open circle), COS-A− supernatant (0.5 ml) (closed square), fibronectin in uncoated dishes (1.6 mg/ml) (triangle) or in dishes precoated with gelatin (closed circle). Beads were also preincubated with COS-A+ supernatant (0.5 ml) and 500 ug of the octamer NGRGDSLA (open square), or 500 ug of the hexamer DESDET. Migration of cells in dishes containing COS-A++DESDET was not significantly different from COS-A+ (open circle). Immunoprecipitation of 0.5 ml of COS-A+ supernatant indicated that it contained approximately 1 to 10 ug of Ap-1.

FIG. 8. Photomicrographs of peritoneal macrophages. Cells that had migrated to the rim of the central well 24 hours after initiation of the migration assays are shown. A: Cells in dishes with central wells containing beads saturated with COS-A+ supernatant. Ingested sepharose beads and the epithelioid appearance of the cells with dendrite-like extrusions are apparent (100× magnification). Sepharose beads added to adherent peritoneal cells in the absence of Ap-1 were not ingested. B: Same as A (200× magnification). C: Cells in dishes with central wells containing beads saturated with COS-A− supernatant (100× magnification). D: Cells in dishes with central wells containing beads saturated with a mixture of COS-A+ supernatant and the RGD octamer representing an excess of about 100:1 octamer:Ap-1 (100× magnification).

Figure 9:
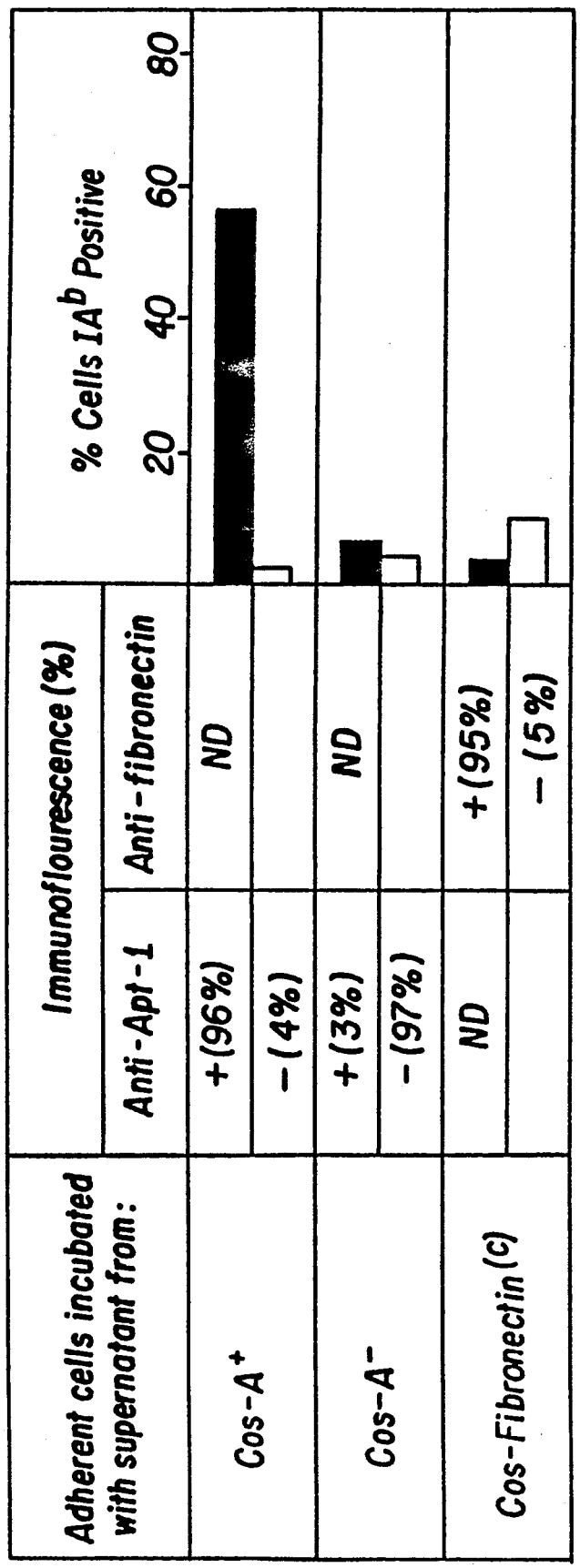

FIG. 9. Indirect immunofluorescence assays of Ap-1 binding and Ia expression. Cells were incubated for 40 minutes with COS-A+ supernatant, COS-A− supernatant, or COS-A− supernatant+1 mg/ml fibronectin ("COS-fibronectin"), and Ap-1 binding was determined by indirect immunofluorescence as described for FIG. 6. Ia expression was detected after incubation with a rat anti-Ia antibody (M5-114), followed by addition of a rhodamine-conjugated goat anti-rat IgG. Cells were counted (10 to 25 random fields under three coverslips/dish) using a fluorescent photomicroscope with barrier filters of 420–490 nm (fluorescein) and 500–590 nm (rhodamine).

Figure 10A:
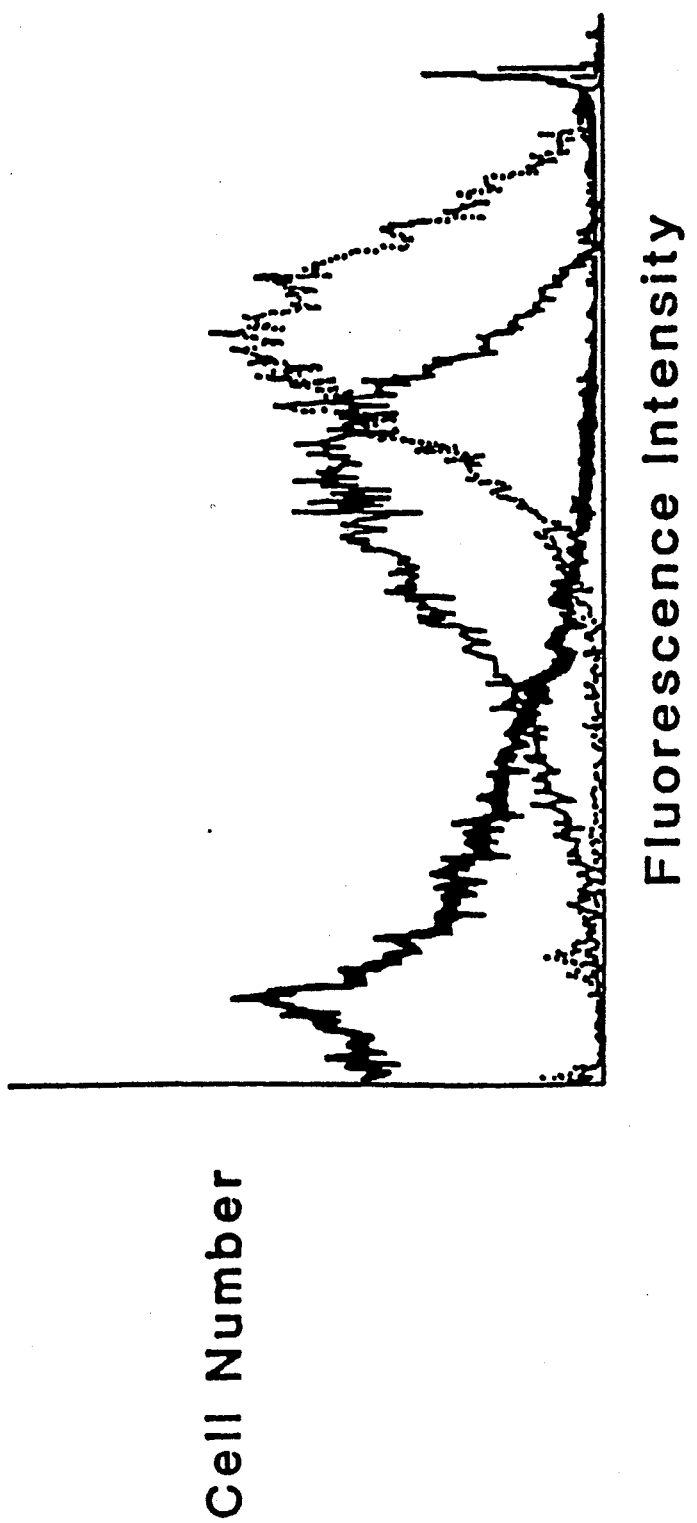

FIG. 10A. Induction of Ia on resident peritoneal macrophages by Ap-1. After incubation of resident peritoneal macrophages with COS-A+ supernatant (final dilution 1:50), gamma-interferon (100 U), or COS-A− supernatant (final dilution 1:10), expression of Ia was determined by FACS analysis as described in Section 6.1.19.2. The FACS profiles for COS-A+ supernatant, COS-A− supernatant, and gamma-interferon treatment are depicted as dashed, bold, and thin lines, respectively.

FIG. 10B. Induction of Ia on a macrophage cell line by Ap-1. The profiles of Ia expression on the macrophage cell line WEHI-3 was determined by FACS analysis as described in Section 6.1.19.2, after incubation with gamma-interferon (thin line), COS-A+ supernatant (bold line), or COS-A− supernatant (dashed line) (at the final concentrations listed for FIG. 10A).

Figure 10C:
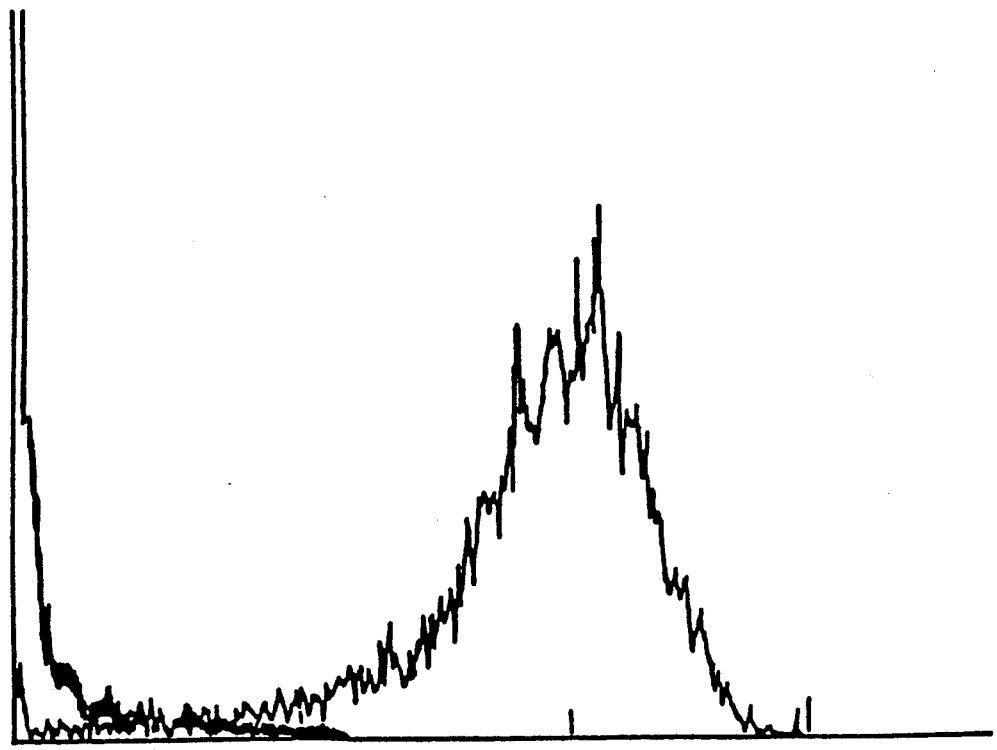

FIG. 10C. Ap-1 does not induce Ia on a B cell line. The FACS profile of Ia expression by the B cell line R8205 after incubation with COS-A+ supernatant (final dilution 1:10) is depicted by a bold line, and the Ia profile of R8205 after incubation with recombinant BSF-1 (approximately 100 ng/ml) is depicted by a thin line. FACS analysis was carried out as described in Section 6.1.19.2.

Figure 11:
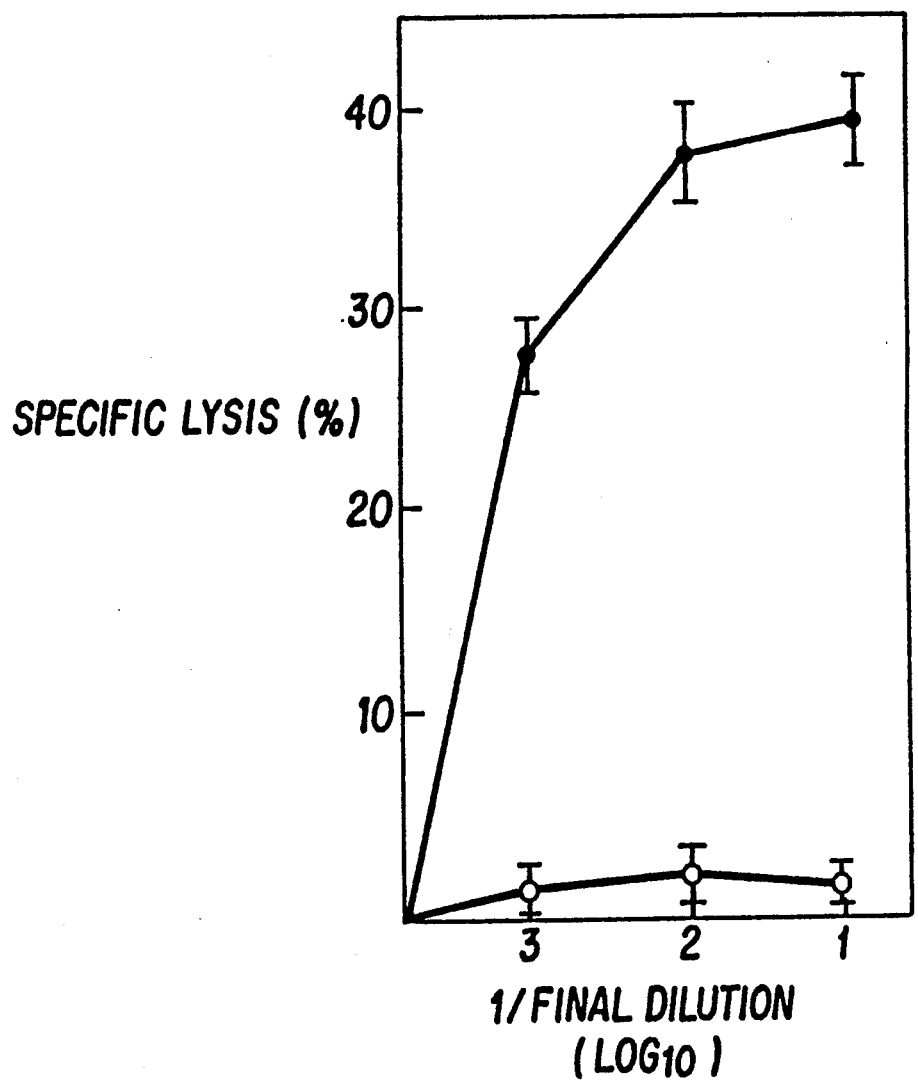

FIG. 11. Enhancement of macrophage tumoricidal activity by supernatants from COS cells transfected with pCD-Ap-1. The indicated final dilutions of COS-A+ supernatant (closed circles) or COS-A− supernatant (open circles) were added to cultures containing resident peritoneal macrophages (RPM) ($10^5$ cells/well) and $^{51}$Cr-labeled EL-4 cells ($10^4$ cells/well). Six hours later, specific lysis of EL-4 tumor cells was determined as described in Section 6.1.22.

Figure 12:
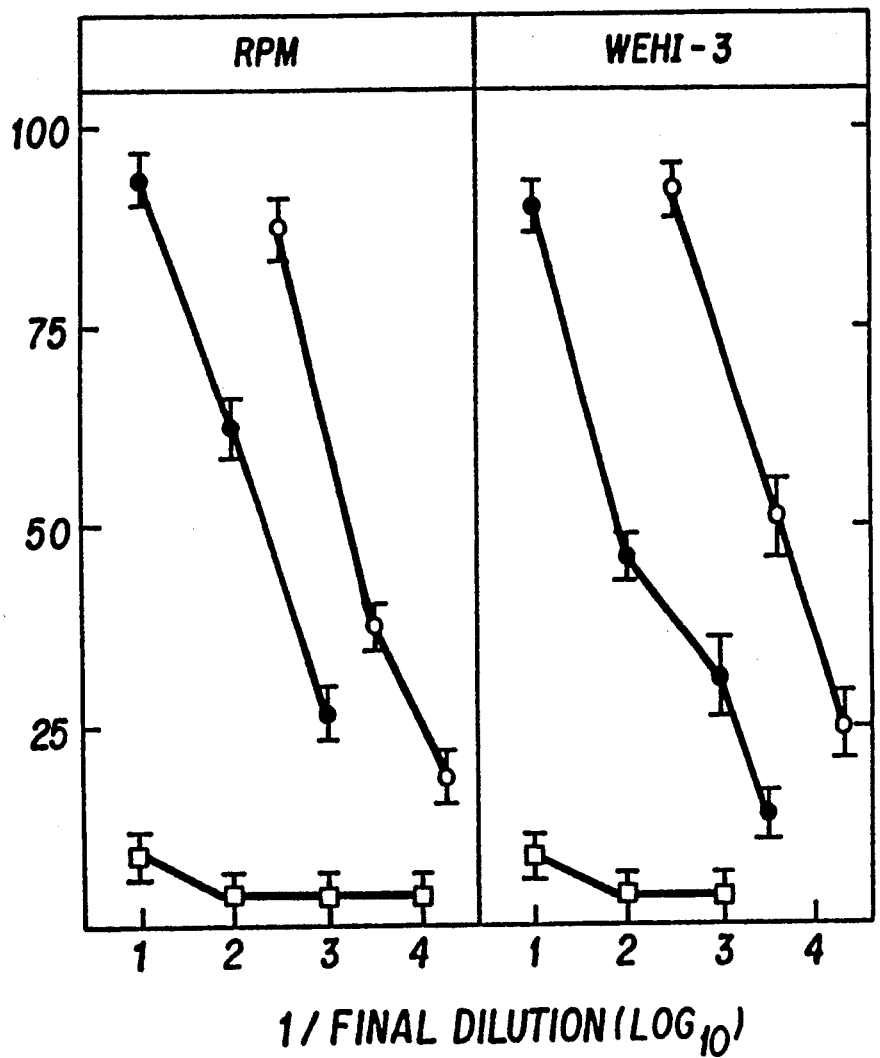

FIG. 12. Induction of macrophage tumoricidal activity by Ap-1. COS-A+ supernatant (closed circles) or COS-A− supernatant (open squares), or Ap-1(Fx5) (open circles) (obtained from COS-A+ supernatant after ion exchange chromatography) were added to RPM cells (left panel) or WEHI-3 cells (right panel), at the final dilutions indicated on the abscissa. After a 12 hour incubation, the cells were washed once. Radiolabelled EL-4 tumor cells were added, and after six hours of incubation, specific lysis of EL-4 cells was measured.

Figure 13:
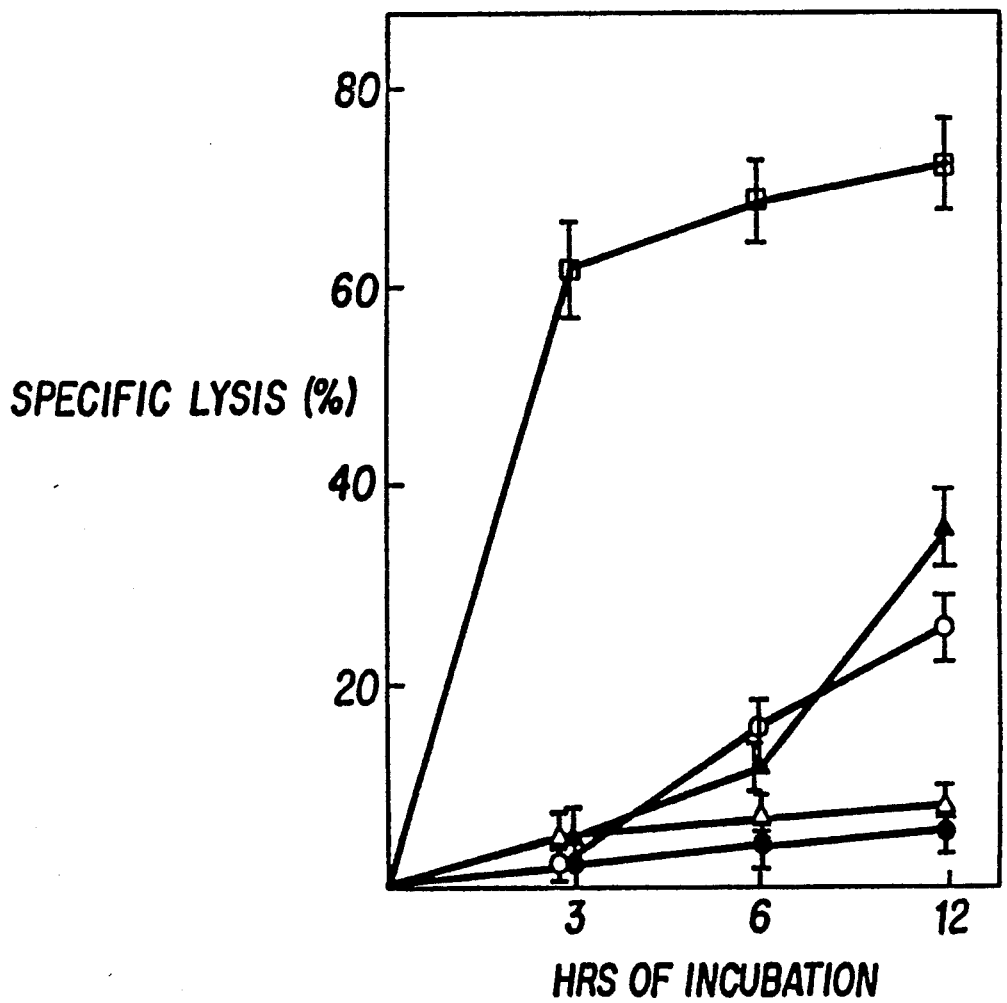

FIG. 13. Kinetics of Ap-1 induction of macrophage cytotoxicity. Resident peritoneal macrophages (RPM) were incubated for the indicated intervals with Ap-1(FxD) (0.25 ug/ml) (closed squares), gamma-interferon (50 ug/ml) (open triangles), COS-A− supernatant (10 ug/ml) (open squares), LPS (1 ug/ml)+gamma-interferon (25 ug/ml) (closed triangles), or Ap-1(FxD) (0.25 ug/ml)+gamma-interferon (0.25 ug/ml) (closed circles). After three washings, tumoricidal activity against EL-4 was measured in a two hour assay. Note the decrease in induction of RPM-mediated tumoricidal activity by Ap-1 (closed squares) in the presence of gamma-interferon (closed circles).

Figure 14:
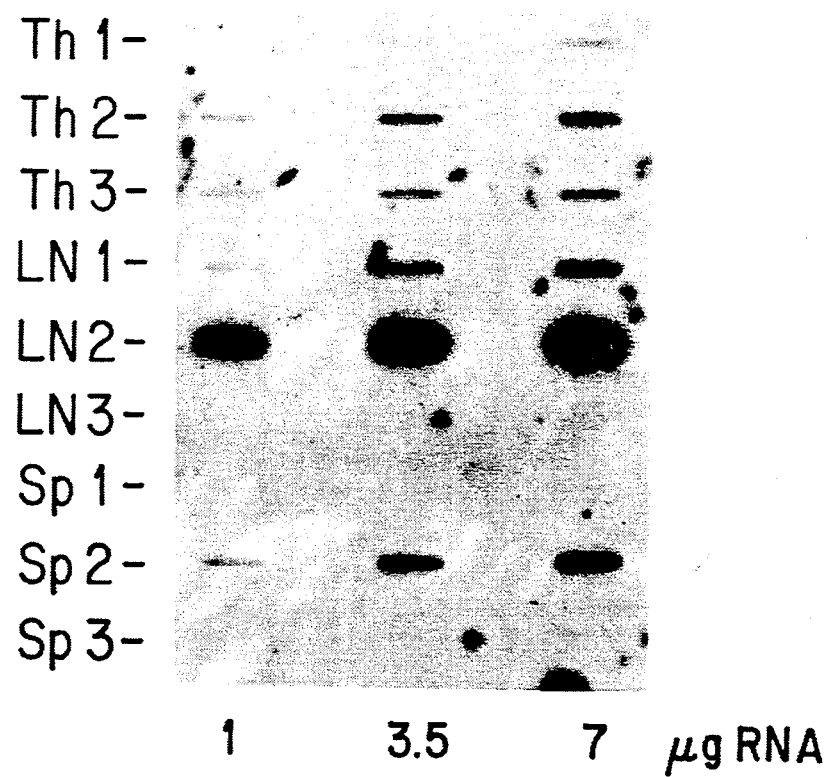

FIG. 14. Analysis of Ap-1 expressed in lymphoid cells of MRL− mice. Total RNA was extracted from thymus (Th), peripheral lymph nodes (LN), and spleen (Sp) from the following donors: 1, MRL +/+ mice 40 weeks after birth; 2, MRL lpr/lpr mice 40 weeks after birth; and 3, MRL lpr/lpr mice 10 weeks after birth. Hybridization of Ap-1 cDNA (XhoI fragment) to the indicated amounts of RNA is shown.

5. DETAILED DESCRIPTION OF THE INVENTION

The present invention relates to genes and their encoded proteins, expressed by lymphoid cells, which induce activation and chemattraction of immunological effector cells. Such proteins, termed Ap-1 (activation protein-1), bind specifically to effector cells such as macrophages and mast cells. The Ap-1 proteins induce phagocytosis, cytotoxicity, and migration of macrophages, and induce hematopoietic progenitor cell differentiation. They have widespread value in immunotherapy and immunodiagnostics, where they can be used in the modulation and/or monitoring of the inflammatory and immune response.

In a particular embodiment of the present invention detailed in the examples sections infra, a murine Ap-1 protein of approximately 60,000 molecular weight and an isoelectric point of about 4.5 is described. Two representative Ap-1 genes, a murine Ap-1 cDNA clone and a human genomic Ap-1 clone, are also described. The murine Ap-1 gene is shown to be expressed at elevated levels in mice with an autoimmune disorder.

5.1. ISOLATION OF THE AP-1 GENE

Any mammalian cell can potentially serve as the nucleic acid source for the molecular cloning of the Ap-1 gene. Isolation of the Ap-1 gene involves the isolation of those DNA sequences which encode a protein displaying Ap-1-associated structure, properties, or activities, e.g., immunological effector cell binding, macrophage activation, macrophage chemattraction, induction of macrophage cytotoxicity, and induction of hematopoietic progenitor cell differentiation (see Section 5.5 and subsections therein, infra). The DNA may be obtained by standard procedures known in the art from cloned DNA (e.g., a DNA "library"), by chemical synthesis, by cDNA cloning, or by the cloning of genomic DNA, or fragments thereof, purified from the desired mammalian cell. (See, for example, Maniatis et al., 1982, Molecular Cloning: A Laboratory Manual, Cold Spring Harbor Laboratory, Cold Spring Harbor, N.Y.; Glover, D. M. (ed.), 1985, DNA Cloning: A Practical Approach, MRL Press, Ltd., Oxford, U.K., Vol. I, II.) Clones derived from genomic DNA may contain regulatory and intron DNA regions, in addition to coding regions; clones derived from cDNA will contain only exon sequences. Whatever the source, the Ap-1 gene should be molecularly cloned into a suitable vector for propagation of the gene.

In the molecular cloning of the gene from genomic DNA, DNA fragments are generated, some of which will encode the desired Ap-1 gene. The DNA may be cleaved at specific sites using various restriction enzymes. Alternatively, one may use DNA in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the Ap-1 gene may be accomplished in a number of ways. For example, if an amount of an Ap-1 gene or its specific RNA, or a fragment thereof, is available and can be purified and labeled, the generated DNA fragments may be screened by nucleic acid hybridization to the labeled probe (Benton, W. and Davis, R., 1977, Science 196:180; Grunstein, M. and Hogness, D., 1975, Proc. Natl. Acad. Sci. U.S.A. 72:3961). If a purified Ap-1-specific probe is unavailable, nucleic acid fractions enriched in Ap-1 may be used as a probe, as an initial selection procedure. As an example (see Section 6.1.5.1, infra), the probe representing T cell cDNA from which B cell messages have been subtracted can be used. It is also possible to identify the appropriate fragment by restriction enzyme digestion(s) and comparison of fragment sizes with those expected according to a known restriction map if such is available. Further selection on the basis of the properties of the gene, or the physical, chemical, or immunological properties of its expressed product, as described infra, can be employed after the initial selection.

The Ap-1 gene can also be identified by mRNA selection by nucleic acid hybridization followed by in vitro translation. In this procedure, fragments are used to isolate complementary mRNAs by hybridization. Such DNA fragments may represent available, purified Ap-1 DNA, or DNA that has been enriched for Ap-1 sequences (e.g., cDNA specific to activated T cells; see Sections 6.1.4 and 6.1.5, infra). Immunoprecipitation analysis or functional assays (e.g., for macrophage attraction, activation, binding) of the in vitro translation products of the isolated mRNAs identifies the mRNA and, therefore, the complementary DNA fragments that contain the Ap-1 sequences. In addition, specific mRNAs may be selected by adsorption of polysomes isolated from cells to immobilized antibodies specifically directed against an Ap-1 protein. A radiolabelled Ap-1 cDNA can be synthesized using the selected mRNA (from the adsorbed polysomes) as a template. The radiolabelled mRNA or cDNA may then be used as a probe to identify the Ap-1 DNA fragments from among other genomic DNA fragments.

Alternatives to isolating the Ap-1 genomic DNA include, but are not limited to, chemically synthesizing the gene sequence itself from a known sequence or making cDNA to the mRNA which encodes the Ap-1 gene. For example, RNA for cDNA cloning of the Ap-1 gene can be isolated from cells including but not limited to immune cells such as T cells and natural killer (NK) cells. Other methods are possible and within the scope of the invention. The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid or pCD/Okayama-Berg plasmid (Okayama, H. and Berg, P., 1983, Mol. Cell. Biol. 3:280–289) derivatives. Recombinant molecules can be introduced into host cells via transformation, transfection, infection, electroporation, etc.

In a particular embodiment, the Ap-1 gene expressed in activated T cells can be cloned by selection from a constructed sublibrary that contains cDNA inserts that are selectively expressed by T cells subsets after activation by antigen or mitogen. Such a procedure is described in Sections 6.1.1 through 6.1.7, infra.

In another embodiment, an Ap-1 genomic clone can be obtained from a genomic library, after selection by hybridization to an Ap-1-homologous nucleic acid sequence (see Section 6.3, infra).

In an alternative method, the Ap-1 gene may be identified and isolated after insertion into a suitable cloning vector, in a "shot gun" approach. Enrichment for the Ap-1 gene, for example, by size fractionation or subtraction of cDNA specific to resting T cells, can be done before insertion into the cloning vector.

The Ap-1 gene is inserted into a cloning vector which can be used to transform, transfect, or infect appropriate host cells so that many copies of the gene sequences are generated. In a specific embodiment, the cloning vector can be the pCD vector (Okayama-Berg vector; Okayama, H. and Berg, P., 1983, Mol. Cell. Biol. 3:280–289). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Such modifications include producing blunt ends by digesting back single-stranded DNA termini, or by filling in the single-stranded termini so that the ends can be blunt-end ligated. Alternatively, any site desired may be produced by ligating nucleotide sequences (linkers) onto the DNA termini; these ligated linkers may comprise specific chemically synthesized oligonucleotides encoding restriction endonuclease recognition sequences. For example, according to the DNA modification procedure of Maniatis, sheared DNA is treated with a restriction methylase (for example, M.EcoRI) and ligated to synthetic DNA linkers for that enzyme. The DNA is then treated with restriction endonuclease to cleave the terminal linkers (but not the modified internal restriction sites) and ligated to the appropriate vector arm. In an alternative method, the cleaved vector and Ap-1 gene may be modified by homopolymeric tailing.

Identification of the cloned Ap-1 gene can be accomplished in a number of ways based on the properties of the DNA itself, or alternatively, on the physical, immunological, or functional properties of its encoded protein. For example, the DNA itself may be detected by plaque or colony nucleic acid hybridization to labelled probes (Benton, W. and Davis, R., 1977, Science 196:180; Grunstein, M. and Hogness, D., 1975, Proc. Natl. Acad. Sci. U.S.A. 72:3961). Alternatively, the presence of the Ap-1 gene may be detected by assays based on properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps; macrophage or mast cell binding, attraction, or activation; sedimentation, or antigenic properties as known for Ap-1. If an antibody to Ap-1 is available, the Ap-1 protein may be identified by binding of labelled antibody to the putatively Ap-1-synthesizing clones, in an ELISA (enzyme-linked immunosorbent assay)-type procedure.

In specific embodiments, transformation of host cells with recombinant DNA molecules that incorporate the isolated Ap-1 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

In a particular embodiment, Ap-1 cDNA clones in a pCD vector (Okayama, H. and Berg, P., 1983, Mol. Cell. Biol. 280–289) can be transfected into COS (monkey kidney) cells for large-scale expression (see Section 6.1.9, infra).

If the ultimate goal is to insert the gene into virus expression vectors such as vaccinia virus or adenovirus, the recombinant DNA molecule that incorporates the Ap-1 gene can be modified so that the gene is flanked by virus sequences that allow for genetic recombination in cells infected with the virus so that the gene can be inserted into the viral genome.

After the Ap-1 DNA-containing clone has been identified, grown, and harvested, its DNA insert may be characterized as to its restriction sites by various techniques known in the art (Maniatis, T., et al., Molecular Cloning, A Laboratory Manual, Cold Spring Harbor Laboratory, Cold Spring Harbor, N.Y. ).

The sequence of the Ap-1 DNA insert can then be determined. Methods by which this may be accomplished include the Maxam-Gilbert procedure (Maxam, A. M. and Gilbert, W., 1980, Meth. Enzymol. 65:499), the Sanger dideoxy chain termination procedure (Sanger, F., et al., 77, Proc. Natl. Acad. Sci. U.S.A. 74:5463), or use of an automatic DNA sequenator (e.g., Applied Biosystems, Foster City, Calif.), etc.

When the genetic structure of the Ap-1 gene is known, it is possible to manipulate the structure for optimal use in the present invention. For example, promoter DNA may be ligated 5' of the Ap-1 coding sequence, in addition to or replacement of the native promoter to provide for increased expression of the protein. Many manipulations are possible, and within the scope of the present invention.

5.2. EXPRESSION OF THE CLONED AP-1 GENE

The nucleotide sequence coding for an Ap-1 protein or a portion thereof, can be inserted into an appropriate expression vector, i.e., a vector which contains the necessary elements for the transcription and translation of the inserted protein-coding sequence. The necessary transcriptional and translation signals can also be supplied by the native Ap-1 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. The expression elements of these vectors vary in their strength and specificities. Depending on the host-vector system utilized, any one of a number of suitable transcription and translation elements may be used. For instance, when cloning in mammalian cell systems, promoters isolated from the genome of mammalian cells (e.g., mouse metallothionein promoter) or from viruses that grow in these cells (e.g., vaccinia virus 7.5K promoter) may be used. Promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where the entire Ap-1 gene including its own initiation codon and adjacent sequences are inserted into the appropriate expression vectors, no additional translational control signals may be needed. However, in cases where only a portion of the Ap-1 coding sequence is inserted, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination).

Expression vectors containing Ap-1 gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to the inserted Ap-1 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes into the vector. For example, if the Ap-1 gene is inserted within the marker gene sequence of the vector, recombinants containing the Ap-1 insert can be identified by the absence of the marker gene function. In the third approach, recombinant expression vectors can be identified by assaying the foreign gene product expressed by the recombinant. Such assays can be based on the physical, immunological, or functional properties of the gene product (see Section 5.5, infra).

Once a particular recombinant DNA molecule is identified and isolated, several methods may be used to propagate it, depending on whether such a recombinant constitutes a self-replicating unit (a replicon). A self replicating unit, e.g., plasmid, virus, cell, etc., can multiply itself in the appropriate cellular environment and growth conditions. Recombinants lacking a self-replicating unit will have to be integrated into a molecule having such a unit in order to be propagated. For example, certain plasmid expression vectors upon introduction into a host cell need to be integrated into the cellular chromosome to ensure propagation and stable expression of the recombinant gene. Once a suitable host system and growth conditions are established, recombinant expression vectors can be propagated and prepared in quantity.

In a particular embodiment detailed in the examples of the present invention, pCD vectors with an Ap-1 cDNA insert can be transfected into COS cells, in which the Ap-1 cDNA insert is expressed to produce the Ap-1 protein. However, the invention is not limited to the expression of Ap-1 from pCD vectors in COS cells. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the chimeric gene product in the specific fashion desired. Expression from certain promoters can be elevated in the presence of certain inducers (e.g., zinc and cadmium ions for metallothionein promoters). Therefore, expression of the genetically engineered Ap-1 protein may be controlled. Furthermore, modifications (e.g., glycosylation) and processing (e.g., cleavage) of protein products may be important for different functions of the protein. Different host cells have characteristic and specific mechanisms for the translational and post-translational processing and modification of proteins. Appropriate cell lines or host systems can be chosen to ensure the desired modification and processing of the heterologous expressed protein. For example, expression in a bacterial system can be used to produce an unglycosylated core protein product, such as the 32 kd Ap-1 protein with the sequence of FIG. 2B. Expression in yeast will produce a glycosylated product. In a particular embodiment, mammalian COS cells can be used to ensure "native" glycosylation of the heterologous Ap-1 protein. Furthermore, different vector/host expression systems may effect processing reactions such as proteolytic cleavages to different extents. For example, the Ap-1 protein of FIG. 2B could be produced without proteolytic cleavage of its signal sequence, thus producing a protein of greater molecular weight than otherwise expected. Thus modifications such as glycosylation, proteolytic cleavages, etc. can be obtained to different degrees, depending on the expression system used; such variously processed proteins may or may not retain one or more of the Ap-1 protein-associated properties, described infra in Section 5.5 and subsections therein. For example, an Ap-1 protein which is inactive in macrophage activation due to a lack of glycosylation or post-translational proteolytic cleavage, yet which still remains macrophage binding ability, can be used as a competitive inhibitor of macrophage activation in vivo. Many such variously processed Ap-1 proteins can be produced and are within the scope of the present invention.

5.3. IDENTIFICATION AND PURIFICATION OF THE EXPRESSED GENE PRODUCT

Once a recombinant which expresses the Ap-1 gene is identified, the gene product should be analyzed. This can be achieved by assays based on the physical, immunological, or functional properties of the product (see Sections 5.4, 5.5, and subsections, infra).

The Ap-1 protein may be isolated and purified by standard methods including chromatography (e.g., ion exchange, affinity, and sizing column chromatography), centrifugation, differential solubility, or by any other standard technique for the purification of proteins. In a specific embodiment, the 60 (approx.) kd Ap-1 protein described in Section 6 infra can be purified by DEAE-cellulose ion exchange chromatography of supernatant fluids of transfected cells expressing a recombinant Ap-1 gene (see Section 6.1.12, infra).

Alternatively, once an Ap-1 protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In particular embodiments of the present invention, such Ap-1 proteins, whether produced by recombinant DNA techniques or by chemical synthetic methods, include but are not limited to those containing, as a primary amino acid sequence, all or part of the amino acid sequence substantially as depicted in FIG. 2B, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are Ap-1 proteins which are differentially modified during or after translation, e.g., by glycosylation, proteolytic cleavage, etc.

5.4 STRUCTURE OF THE AP-1 GENE AND PROTEIN

The structure of the Ap-1 gene and protein can be analyzed by various methods known in the art.

5.4.1. GENETIC ANALYSIS

The cloned DNA or cDNA corresponding to the Ap-1 gene can be analyzed by methods including but not limited to Southern hybridization (Southern, E. M., 1975, J. Mol. Biol. 98:503-517), Northern hybridization (see e.g., Freeman et al., 1983, Proc. Natl. Acad. Sci. U.S.A. 80:4094-4098), restriction endonuclease mapping (Maniatis, T., 1982, Molecular Cloning, A Laboratory Manual, Cold Spring Harbor Laboratory, Cold Spring Harbor, New York), and DNA sequence analysis. Southern hybridization with the Ap-1-specific probe can allow the detection of the Ap-1 gene in various cell types. Northern hybridization analysis can be used to determine the expression of the Ap-1 gene. Various cell types, at various states of development or activity can be tested for Ap-1 expression. Such a technique and its results, demonstrating Ap-1 expression by transfected COS cells, are described in Sections 6.1.10 and 6.5, infra. The stringency of the hybridization conditions for both Southern and Northern hybridization can be manipulated to ensure detection of nucleic acids with the desired degree of relatedness to the specific Ap-1 probe used.

Restriction endonuclease mapping can be used to roughly determine the genetic structure of the Ap-1 gene, and the extent of homology between the Ap-1 9 ene and other genes. In a particular embodiment, cleavage with restriction enzymes can be used to derive the restriction map shown in FIG. 2A, infra. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499-560), the Sanger dideoxy method (Sanger, F., et al., 1977, Proc. Natl. Acad. Sci. U.S.A. 74:5463), or use of an automated DNA sequenator (e.g., Applied Biosystems, Foster City, Calif.). The cDNA sequence of a representative member of the Ap-1 family comprises the sequence substantially as depicted in FIG. 2B, and detailed in Section 6.4, infra.

5.4.2. PROTEIN ANALYSIS

The amino acid sequence of the Ap-1 protein can be derived by deduction from the DNA sequence, or alternatively, by direct sequencing of the protein, e.g., with an automated amino acid sequencer. The amino acid sequence of a representative member of the Ap-1 family comprises the sequence substantially as depicted in Figure B, and detailed in Section 6.4, infra.

The Ap-1 protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the Ap-1 protein and the corresponding regions of the gene sequence which encode such regions. A hydrophilicity profile of a representative member of the Ap-1 family is depicted in FIG. 3A.

Secondary structural analysis (Chou, P. and Fasman, G., 1974, Biochemistry 13:222) can also be done, to identify regions of Ap-1 that assume specific secondary structures.

Other methods of structural analysis can also be employed. These include but are not limited to X-ray crystallography (Engstom, A., 1974, Biochem. Exp. Biol. 11:7-13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. PROPERTIES OF AP-1

The Ap-1 gene encodes an extremely hydrophilic secreted protein, which binds specifically to several subsets of immunological effector cells such as macrophages and mast cells. The Ap-1 protein mediates the chemattraction and activation of immunological effector cells (e.g., macrophages), and promotes the differentiation of hematopoietic progenitor cells such as the CFU-GM. Several biological subsequences of Ap-1 appear to mediate specific activities of the molecule; for example, Ap-1 contains an arginine-glycine-aspartic acid (RGD) subsequence that contributes to the protein's binding to specific receptors on mast cells and macrophages. A detailed discussion of the biologically active subsequences and activities of the Ap-1 protein, a 32 kd core protein (pI of 4.1) that is glycosylated to a molecular weight of approximately 60 kd, which is rapidly transcribed after activation of T lymphocytes, is found in Section 6 and its subsections, infra.

The Ap-1 protein appears to be expressed at relatively high levels in animals with an autoimmune disorder (see Section 6.9, infra); its various activities are thus implicated in the etiology and/or manifestations of such disorders.

5.5.1. IMMUNOLOGICAL EFFECTOR CELL BINDING

Ap-1 binds specifically to several subsets of immunological effector cells including macrophages, thymocytes, and mast cells, but not to B lymphocytes nor non-lymphoid cells such as fibroblasts (see Sections 6.7.1 and 6.7.2, infra). The arg-gly-asp (RGD) subsequence of Ap-1 contributes to the protein's binding to specific receptors on the immunological effector cells.

Any procedure known in the art may be used to assay Ap-1 binding to various cells. As an example, cells in suspension may be incubated with labelled Ap-1, washed, and analyzed by fluorescence activated cell sorting (for a fluorescent label) or liquid scintillation counting (for a radioactive label; see Section 6.1.18, infra). Alternatively, the cells which bind labelled Ap-1 may be fixed and examined under the microscope for the presence of the label. Binding may also be determined by quantifying attachment of cells to surfaces (e.g., dishes, beads) coated with Ap-1 (see e.g., Bevilacqua, M. P., et al., 1981, J. Exp. Med. 153:42-60). Other binding assays are known and are within the scope of the invention.

The binding assays may also be carried out with fragments or specific subsequences of Ap-1, or modifications or analogues thereof, in competitive and noncompetitive assays, in attempts to more precisely define the protein domain(s) which mediate cell binding. In a specific embodiment, an Ap-1 subsequence containing the RGD tripeptide, such as NGRGDSLA, can be tested for its binding to immunological effector cells, or, for its inhibition of Ap-1 binding to immunological effector cells (see FIG. 6, Section 6.7.2, infra). In a particular embodiment employing the Ap-1 protein described in Section 6, infra, an excess amount of the octapeptide NGRGDSLA relative to Ap-1, can block Ap-1 binding to cells (FIG. 6).

5.5.2. IMMUNOLOGICAL EFFECTOR CELL ACTIVATION

Ap-1 mediates the activation of immunological effector cells such as macrophages. Upon binding of Ap-1, macrophages demonstrate morphological changes consistent with activation, acquire increased phagocytic activity, increased cytotoxicity toward target cells such as tumor cells, and express class II MHC (Ia) molecules on their cell surface (see Sections 6.8.2, through 6.8.4 infra).

Once purified, Ap-1 or a subsequence, derivative, or analogue thereof, can be tested for effects on immunological effector cell activation by numerous assays known in the art. For example, induction of Ia expression can be assayed for by binding of labelled anti-Ia antibody (see e.g., Sections 6.1.19, 6.8.2, and subsections therein). Phagocytic activity can be assayed by observing under a microscope the number of latex beads ingested by macrophages (see Section 6.8.3, infra). Other assays are known and may be used (see e.g., Wright, S. D. and Meyer, B. C., 1985, J. Exp. Med. 162:762-767; Fidalgo B. V. and Najjar, V. A., 1967, Biochemistry 6(11):3386-3392, for assays of phagocytosis).

5.5.3. IMMUNOLOGICAL EFFECTOR CELL CHEMATTRACTION

Ap-1 is chemotactic for immunological effector cells such as macrophages (see Section 6.8.1, infra). Ap-1 attracts these cells, inducing their migration. The chemattraction of immunological effector cells by Ap-1 can be demonstrated by observing migration in culture dishes across a gradient formed by Ap-1, in a visual dish assay (see Section 6.1.21.1.), under agarose, or in a modified Boyden chamber apparatus (see Section 6.1.21.2), etc. Other methods of measuring chemotaxis are also known and may be used (e.g., Altman, L. C., et al., 1973, J. Immunol. 110(3):801-810; Cohen, S. and Ward, P. A., 1971, J. Exp. Med. 133(1):133-146).

Purified Ap-1 proteins, subsequences, derivatives, or analogues thereof, can be tested in chemotaxis assays for their effect on immunological effector cell migration. The induction of macrophage migration toward the Ap-1 molecule of FIG. 2B is accompanied by acquisition of phagocytic activity and expression of class II MHC molecules on the cell surface (see Sections 6.8.1 through 6.8.3). These changes are a direct result of binding of the soluble Ap-1 to receptors on the macrophages; a synthetic peptide containing the RGD subsequence of the Ap-1 (NGRGDSLA) can inhibit the Ap-1 binding and Ap-1-induced cell migration (see Section 6.8.1).

5.5.4. INDUCTION OF IMMUNOLOGICAL EFFECTOR CELL CYTOTOXICITY

Ap-1 is able to induce macrophage cytotoxicity toward target cells. Such target cells can include but are not limited to pathogenic microorganisms, tumor cells, infected cells, or virally transformed cells. Treatment with Ap-1 causes an increase in macrophage cytotoxicity toward target cells to an even greater extent than that observed upon gamma-interferon treatment (see Section 6.8.4 infra). Thus, Ap-1 has a relatively high degree of specific activity in induction of macrophage cytotoxicity. Furthermore, induction of cytotoxicity by Ap-1 occurs in the absence of an added cofactor. In contrast, optimal induction by gamma-interferon requires the presence of a cofactor, or second signal, such as LPS, endotoxin, or phorbol esters (see, e.g., Celada, A., et al., 1984, J. Exp. Med. 160:55-74).

5.5.5. INDUCTION OF GRANULOCYTE/MONOCYTE PROGENITOR CELL DIFFERENTIATION

Ap-1 induces the differentiation of hematopoietic progenitor cells. An in vivo colony forming assay such as described in Section 6.1.23infra can be used to demonstrate enhanced production of granulocyte/monocyte cells from hematopoietic progenitor cells present in bone marrow, upon Ap-1 treatment (see Section 6.8.5, infra). In such an assay, Ap-1 can be shown to induce granulocyte/monocyte progenitor cell differentiation at a level comparable to that of G/M CSF.

5. 6. ANTI-AP-1 ANTIBODY PRODUCTION

Antibodies can be produced which recognize the Ap-1 protein. Such antibodies can be polyclonal or monoclonal.

Various procedures known in the art may be used for the production of polyclonal antibodies to Ap-1. In a particular embodiment, a procedure for producing rabbit polyclonal antibodies to the Ap-1 molecule substantially as depicted in FIG. 2B is described in Section 6.1.15, infra. For the production of antibody, various host animals can be immunized by injection with the native Ap-1 protein, or a synthetic version, or fragment thereof, including but not limited to rabbits, mice, rats, etc. Various adjuvants may be used to increase the immunological response, depending on the host species, and including but not limited to Freund's (complete and incomplete), mineral gels such a aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

A monoclonal antibody to Ap-1 can be prepared by using any technique which provides for the production of antibody molecules by continuous cell lines in culture. These include but are not limited to the hybridoma technique originally described by Kohler and Milstein (1975, Nature 256:495-497), and the more recent human B-cell hybridoma technique (Kozbor et al., 1983, Immunology Today 4:72) and EBV-transformation technique (Cole et al., 1985, Monoclonal Antibodies amd Cancer Therapy, Alan R. Liss, Inc., pp. 77-96).

Antibody fragments which contain the idiotype of the molecule could be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the 2 Fab or Fab fragments which can be generated by treating the antibody molecule with papain and a reducing agent.

5.7. AP-1-RELATED DERIVATIVES, ANALOGUES, AND PEPTIDES

The production and use of derivatives, analogues, and peptides related to Ap-1 are also envisioned, and within the scope of the present invention. Such derivatives, analogues, or peptides which have the desired immunogenicity or antigenicity can be used, for example, in immunoassays, for immunization, therapeutically, etc. Such molecules which retain, or alternatively inhibit, a desired Ap-1 property, e.g., immunological effector cell binding, activation, and/or chemattraction, can be used as inducers, or inhibitors, respectively, of such property. Derivatives, analogues, or peptides related to Ap-1 can be tested for the desired activity by procedures known in the art, including but not limited to the effector cell binding, activation, chemattraction, and other assays listed in Sections 5.5.1 through 5.5.5, and 5.8.

The Ap-1-related derivatives, analogues, and peptides of the invention can be produced by various methods known in the art. The manipulations which result in their production can occur at the gene or protein level. For example, the cloned Ap-1 gene can be modified by any of numerous strategies known in the art (Maniatis, T., et al., 1982, Molecular Cloning, A Laboratory Manual, Cold Spring Harbor Laboratory, Cold Spring Harbor, N.Y.). The Ap-1 sequence can be cleaved at appropriate sites with restriction endonuclease(s), isolated, and ligated in vitro. If cohesive termini are generated by restriction endonuclease digestion, no further modification of DNA before ligation may be needed. If, however, cohesive termini of the Ap-1 DNA are not available for generation by restriction endonuclease digestion, or different sites other than those available are preferred, any of numerous techniques known in the art may be used to accomplish ligation, at the desired sites. For example, cleavage with a restriction enzyme can be followed by modification to create blunt ends by digesting back or filling in single-stranded DNA termini before ligation. Alternatively, the cleaved ends of the Ap-1 DNA can be "chewed back" using a nuclease such as nuclease Bal 31, exonuclease III, lambda exonuclease, mung bean nuclease, or T4 DNA polymerase exonuclease activity, to name but a few, in order to remove portions of the sequence. An oligonucleotide sequence which encodes the desired restriction site (a "linker") can be ligated onto the DNA. In the production of the gene encoding a derivative, analogue, or peptide related to Ap-1, care should be taken to ensure that the modified gene remains within the same translational reading frame as Ap-1, uninterrupted by translational stop signals, in the gene region where the desired Ap-1-specific activity is encoded.

Additionally, the Ap-1 gene can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551), use of TAB ® linkers (Pharmacia), etc. For example, a mutation that introduces a premature termination codon into the Ap-1 gene, downstream of the RGD-encoding sequence, may be used to produce a gene encoding a short peptide with macrophage binding or activation activity.

Manipulations of the Ap-1 sequence may also be made at the protein level. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc. For example, production in the presence of tunicamycin, or cleavage with $NaBH_4$, can be used to obtain an Ap-1 protein lacking carbohydrate residues, as judged by molecular size and spectrophotometric analysis.

In addition, analogues and peptides related to Ap-1 can be chemically synthesized. For example, a peptide corresponding to a portion of Ap-1 which mediates the desired activity can be synthesized by use of a DNA synthesizer (e.g., Applied Biosystems Model 380A). In a specific embodiment, the peptide NGRGDSLA can be constructed.

5.8. USES OF AP-1

5.8.1. MODULATION OF IMMUNOLOGICAL EFFECTOR CELL RESPONSES

The Ap-1 proteins of the present invention can be therapeutically useful in the modulation of effector cell functions mediated by Ap-1. Such functions include but are not limited to effector cell binding, activation, chemattraction, and induction of cytotoxicity, and induction of granulocyte/monocyte progenitor cell differentiation. The Ap-1 proteins of the present invention have therapeutic value for many of the diseases or disorders associated with such functions, such as immune or inflammatory disorders. The Ap-1 molecule, a subsequence, derivative, or analogue thereof, or an antibody to Ap-1, can be used for treatment, in instances where, for example, an enhancement of the immune or inflammatory response, or of macrophage cytotoxicity, or of granulocyte/monocyte progenitor cell differentiation is desired. For example, various disorders (e.g., immunodeficiencies, cancers) can be teated by Ap-1 proteins in order to increase immune responsiveness. The enhancement of immunity can be achieved by an Ap-1-mediated phagocytic activation of immunological effector cells, increase of macrophage cytotoxicity, induction of hematopoiesis, etc. In another embodiment, Ap-1, or an analogue, derivative, or subsequence thereof which is demonstrated to promote immunological effector cell chemotaxis and activation, can be targeted to an in vivo site of tumor growth or pathogenic microorganism infection, where it will induce effector cell migration and protective activity. For example, conjugation of Ap-1 with an anti-tumor antibody or anti-pathogen antibody can be used to effect proper targeting of the Ap-1 molecule.

Various delivery systems are known and can be used for delivery of Ap-1 and related molecules, e.g., encapsulation in liposomes, expression by bacteria, etc. Other methods of introduction include but are not limited to intradermal, intramuscular, intraperitoneal, intravenous, subcutaneous, and intranasal routes.

In another embodiment of the invention, Ap-1, a related molecule, or an antibody to Ap-1, which is shown to inhibit a response mediated by immunological effector cells such as macrophages, can be used to prevent or treat diseases or disorders associated with a detrimental inflammatory or immune response. For example, Ap-1 or a related molecule (e.g., subsequence, derivative, analogue, variant in glycosylation) which binds to immunologic effector cells yet does not induce an inflammation-promoting response in the cell, can be used to effectively "compete" out binding of the native Ap-1 to the effector cell, thus preventing the native molecule's contribution to the inflammatory response. In one embodiment, such a molecule may potentially be obtained by $NaBH_4$ cleavage or metabolic synthesis with tunicamycin, producing a Ap-1 protein without carbohydrate residues, that may, for example, bind to immunological effector cells yet exhibit no biological activity (and would thus be an antagonist of the native Ap-1 protein's function). In a similar fashion, anti-Ap-1 antibody can be administered in vivo to reduce inflammation-promoting activity of the native Ap-1, either by direct inactivation, or by steric hindrance of the interaction of the Ap-1 with immunological effector cells.

Various diseases and disorders associated with inflammation, such as allergies, autoimmune disorders, and other disorders due to non-specific or undesirable activation of the immune system, can be treated with Ap-1 or related molecules or anti-Ap-1 antibodies which decrease the inflammatory response in vivo. Such diseases and disorders include but are not limited to rheumatoid arthritis, lupus erythematosis, multiple sclerosis, glomerulonephritis, pulmonary disorders, primary biliary cirrhosis inflammation, etc. For example, as described in Section 6.9, infra, Ap-1 is expressed at relatively high levels in mice with an autoimmune disorder; it is possible that treatment with an antagonist of Ap-1 function may prove to be valuable in treatment of such disorders.

5.8.2. ASSAYS

5.8.2.1. IMMUNOASSAYS

Ap-1 proteins, analogues, derivatives, and subsequences thereof, and anti-Ap-1 antibodies, have uses in immunoassays. Such immunoassays can be used in the monitoring of inflammatory responses, for the assay of Ap-1-related activities putatively associated with certain molecules, etc. For example, as a specific embodiment, antibody to Ap-1 can be used to assay in a patient tissue or serum sample for the presence of Ap-1, as an indicator of an ongoing inflammatory response, or to diagnose certain disorders (e.g., autoimmune) associated with increased expression of Ap-1, etc. In a particular embodiment in which the level of secreted Ap-1 is used as a diagnostic or prognostic indicator of an autoimmune disease such as systemic lupus erythematosis, the level of Ap-1 protein present in a serum sample from a patient can be measured.

The immunoassays which can be used include but are not limited to competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays, and immunoelectrophoresis assays, to name but a few.

5.8.2.2. HYBRIDIZATION ASSAYS

Ap-1 genes and related nucleic acid sequences and subsequences, including complementary sequences, can be used in hybridization assays. Such hybridization assays can be used to monitor inflammatory or immune responses associated with Ap-1 expression, to diagnose certain disease states associated with changes in Ap-1 expression, etc. For example, total RNA in a patient sample can be assayed for the presence of Ap-1 mRNA, where the presence or amount of Ap-1 mRNA is indicative of a certain state of immune activation or of disease. In particular, total RNA from a patient sample can be hybridized to Ap-1 cDNA or a fragment thereof, in a "slot-blot" assay as described in Section 6.1.11.

6. ISOLATION AND CHARACTERIZATION OF AN AP-1 PROTEIN PRODUCED BY T LYMPHOCYTES

In the examples herein, we describe the isolation and characterization of a murine Ap-1 protein of approximately 60,000 molecular weight and an isoelectric point of about 4.5. Two Ap-1 genes, a murine Ap-1 cDNA clone and a human genomic clone, are also described. The murine Ap-1 gene is shown to be expressed at elevated levels in mice with an autoimmune disorder.

6.1. EXPERIMENTAL PROCEDURES

6.1.1. T CELL CLONES

The derivation, characterization, and maintenance of the T cell clones have been previously described (Clayberger, C., et al., 1983, J. Exp. Med. 157:1906–1917). Briefly, Cl.Lyl-Tl, Cl.Lyl-N5, and Cl.Lyl-S1 are inducer T cell clones specific for trinitrophenyl (TNP), 4-hydroxy-3-nitrophenyl (NP)-ovalbumin, and I-A$^b$, respectively (id.; Clayberger, C., et al., 1984, J. Immunol. 132:2237–2243). Cl.NK-11 is a natural killer cell clone (Nabel, G., et al., 1981, Proc. Natl. Acad. Sci. U.S.A. 78:1157–1161). The inducer T cell clones were maintained by weekly activation with antigen and irradiated (1800R) spleen cells, followed by culturing in concanavalin A (ConA)-depleted splenocyte conditioned medium (DCM). Cells were considered to be in the resting state when they ceased proliferating in response to DCM 2-4 weeks after antigenic stimulation. Cl.NK-11 was derived in ConA-containing splenocyte conditioned medium, and after approximately 6 months in culture was subsequently grown in DCM. Tumor cell lines were as described (Freeman, G. J., et al., 1983, Proc. Natl. Acad. Sci. U.S.A. 80:4094–4098).

6.1.2. ACTIVATION OF T CELL CLONES FOR cDNA LIBRARY PREPARATION

Resting T cell clones were activated by the addition of ConA to 1 ug/ml and 12-0-tetradecanoylphorbol 13-acetate (TPA) to 20 ng/ml. Cells were harvested for RNA extraction after 15–23 hours.

6.1.3. RNA ISOLATION

RNA was isolated by the procedure of Chirgwin et al. (1979, Biochemistry 18:5294–5299) as modified by Freeman et al. (1983, Proc. Natl. Acad. Sci. U.S.A. 80:4094–4098).

6.1.4. cDNA SYNTHESIS

Using poly(A)+ RNA isolated from the T cell clone Cl.Lyl-Tl 22 hours after ConA activation, $^{32}$P-labeled cDNA was synthesized as described previously (Freeman et al., 1983, Proc. Natl. Acad. Sci. U.S.A. 80:4094–4098), with the modification that 50 ug/ml of actinomycin D was included in the reaction. The RNA template was removed by alkaline hydrolysis and the cDNA was freed of unincorporated nucleotide triphosphates by three cycles of ethanol precipitation in the presence of 2M ammonium acetate.

6.1.5. cDNA HYBRIDIZATIONS

6.1.5.1. PREPARATION OF A PROBE SPECIFIC FOR T LYMPHOCYTE GENES

To prepare a probe specific for T lymphocyte genes (T-B cDNA), $^{32}$P-labeled cDNA was synthesized as described in Section 6.1.4 and hybridized with B cell mRNA and fibroblast mRNA. Hybridizations were performed according to Alt et al. (1978, J. Biol. Chem. 253:1357-1370) and Mather et al. (1981, Cell 23:369-378). Briefly, poly(A)+ RNA (each in 6-fold excess over the amount of mRNA used to make the cDNA) from L cells (a fibroblast tumor) and 2PK3 (a B cell lymphoma) was hybridized to the $^{32}$P-labeled cDNA until a Rot (annealing value) of 5,200 mole-sec/-liter was attained. Single-stranded and double-stranded nucleic acids were separated by hydroxyapatite chromatography (Freeman, G. J., et al., 1983, Proc. Natl. Acad. Sci. U.S.A. 80:4094-4098). The single-stranded cDNA was hybridized with poly(A)+ NA from MOPC 315 (a B cell myeloma) and the single-stranded fraction was isolated by hydroxyapatite chromatography (to yield "T-B subtracted probe").

6.1.5.2. SOUTHERN BLOTTING

Southern blots were performed as described by Gatti et al. (1984, Biotechniques 2:148-155).

6.1.6 cDNA LIBRARY PREPARATION

Using 5 ug of poly(A)+ RNA from Cl.Lyl-T1, 22 hours after ConA activation, a cDNA library of $3.8 \times 10^5$ independent clones was constructed in the pCD vector, according to Okayama and Berg (1982, Mol. Cell. Biol. 2:161-170; 1983, Mol. Cell. Biol. 3:280-289). A 0.5 to 20 kilobase pair (kb) cDNA insert size-selected sublibrary was prepared (Shen, F.-W., et al., 1985, Proc. Natl. Acad. Sci. U.S.A. 82:7360-7363).

6.1.7. COLONY HYBRIDIZATION

A size-selected sublibrary of approximately 9,800 clones (inserts ranging from 0.5 to 20 kb) was sparsely plated onto nitrocellulose filters, and allowed to grow to a width of 0.5 mm under ampicillin selection. The clones were then replica-plated onto nitrocellulose, amplified by chloramphenicol treatment, and prepared for hybridization (Maniatis, T., et al., 1982, Molecular Cloning: A Laboratory Manual, Cold Spring Harbor Laboratory, Cold Spring Harbor, N.Y.). Colonies hybridizing to the T-B subtracted probe were further analyzed by restriction enzyme digestions, cross-hybridization of their cDNA inserts, and Northern blot hybridization using RNA from B cells and from resting and activated T cells.

6.1.8. NUCLEOTIDE SEQUENCE DETERMINATION

The nucleotide sequence of the cDNA insert was determined by the procedure of Maxam and Gilbert (1980, Meth. Enzymol. 65:499-560).

6.1.9. TRANSFECTIONS AND LABELLING OF CELLS

COS 7m6 cells were plated at a density of $1 \times 10^6$ cells per 150 mm dish in 10 ml DMEM (Dulbecco's Minimal Essential Medium) with 10% fetal bovine serum. Twenty-four hours later, the cells were washed twice with phosphate-buffered saline (PBS). Each dish received 6 ug DNA in 5 ml of a solution that contained 250 ug/ml DEAE-dextran in DMEM (Queen, C. and Baltimore, D. 1983, Cell 33:741-748). Dishes were incubated at 37° C. in 5% $CO_2$. After 3-4 hours, the solution was removed, the cells were incubated with 5 ml of 10% dimethyl sulfoxide in DMEM for 10 minutes, then washed with DMEM, and incubated in regular medium at 37° C. in 5% $CO_2$. The media was replaced every 24 hours, and supernatant fluids were harvested between 48-72 hours.

At 72 hours, the cells were internally labeled. They were washed once with DMEM, and were incubated with 1% BSA in media deficient in non-essential amino acids and methionine at 37° C. for two hours before labelling. For labelling, a solution containing 15 uCi/ml each of $^{14}$C-labelled glutamine, $^{14}$C-aspartic acid, and $^{14}$C-glutamic acid (specific activity of 200 to 500 Ci/-mol), or 25 uCi/ml $^{35}$S-methionine, was added. Cells were labelled for 4-6 hours.

Concentration of protein was measured by spectrophotometry at 280 nm. Trichloroacetic acid (TCA)-insoluble counts were determined by precipitation of protein with 10% TCA, followed by washing twice with cold acetone, air-drying, and addition to 50 mm Tris solution containing 1% SDS before liquid scintillation counting (Fresno, M., et al., 1981, J. Exp. Med. 153:1260-1274).

For analysis of binding and biological activities of Ap-1, assays were performed using COS cell supernatant obtained 72 hours after transfection with pCD-Ap-1.

6.1.10. NORTHERN BLOTTING

RNA samples (5 ug polyA+ RNA) were electrophoresed on formaldehyde-agarose gels as described (Freeman, G. J., et al., 1983, Proc. Natl. Acad. Sci. U.S.A. 80:4094-4098). Briefly, RNA was dissolved in double-distilled $H_2O$, and 20 ul of sample buffer and 15 ul of loading buffer were added. The mixture was incubated at 65° C. for 15 minutes before loading on a 1.5% agarose gel containing 6% formaldehyde (id.). The gel was subjected to 100 V constant current for 2 to 3 hours, stained with ethidium bromide, and photographed under ultraviolet light. The mobilities of the 18S and 28S ribosomal subunits were noted. The gel was subsequently washed in the following solutions: 50 mM NaOH, 10 mM NaCl; 100 mM Tris pH 7.5; and $20 \times SSC$. The RNA samples were then transferred overnight from the gel to nitrocellulose paper in the presence of $20 \times SSC$. The nitrocellulose paper was then baked at 80° C. in a vacuum oven for 2 hours.

$^{32}$P-labeled Ap-1 cDNA probe was derived by XhoI digestion of pCD-Ap-1, and isolation of the 1.5 kb Ap-1 insert by electrophoresis on a 1% agarose gel. After electroelution (Elutrap, Schleicher & Shuell), the cDNA insert was precipitated with 0.3M NaCl and 2 volumes of 95% ethanol. The DNA pellet was resuspended in sterile $H_2O$ and nick-translated (alpha-$^{32}$-P-dCTP, New England Nuclear). Hybridization to the $^{32}$P-nick-translated probe was carried out at 68° C. for 12 hours, and was followed by several washings in $2 \times SSC$, 0.1% SDS at 68° C. to remove non-specific hybrids

6.1.11. SLOT BLOT ANALYSIS FOR EXPRESSION OF AP-1 RNA

RNA was extracted as described supra (Section 6.1.3), and was blotted onto nitrocellulose filters according to Maniatis et al. (1982, Molecular Cloning, A Laboratory Manual, Cold Spring Harbor Laboratory, Cold Spring Harbor, N.Y.).

6 1 12. ANALYSIS OF RECOMBINANT AP-1

Supernatant fluids were analyzed by ion-exchange chromatography, isoelectric focusing, and electrophoresis on polyacrylamide gels as described previously (Fresno, M., et al., 1981, J. Exp. Med. 153:1260–1274; Fresno, M., et al., 1982, Cell 30:707–713).

Briefly, 100 ml of COS-A+ or COS-A− supernatant fluids from cells transfected as described supra were ultracentrifuged (100,000×g; 30 minutes) and concentrated 20-fold before dialysis against a buffer containing 2.5% glycerol, 0.01M 2-mercaptoethanol, 0.01M NaCl, and Tris-HCl, pH 6 (sample buffer). The material was loaded onto a 50 ml DE-52 (Pharmacia) (DEAE-cellulose ion exchange chromatography) column and eluted at 20 ml/hour. After elution with 200 ml sample buffer, the column was sequentially eluted with 100 ml of buffer containing 0.1M, 0.5M, and 1M NaCl. The material that was sequentially eluted at different molar concentrations was pooled. Aliquots of the pooled material were analyzed on isoelectric focusing gels (Fresno, M., et al., 1982, Cell 30:707–713), lyophilized, and dissolved in 0.5 ml $H_2O$ before electrophoresis in 10% SDS polyacrylamide gels (id.), and tested for macrophage-activating activity (see infra).

6.1.13. TWO DIMENSIONAL GEL ELECTROPHORESIS

Two dimensional gel electrophoresis was performed essentially by the method of O'Farrell (O'Farrell, P. H., 1975, J. Biol. Chem. 205:4007–4021), modified as described below:

Briefly, $1.5 \times 10^5$ cpm of $^{35}S$-methionine-labelled proteins were loaded onto an isoelectric focusing tube gel (pH 3–10, 1.0×110 mm) from the cathodic end and focused for 2.5 hours at 400 V. The time for the non-equilibrium pH gradient electrophoresis was reduced to 1.5–2.0 hours from 6 hours to allow analysis of acidic proteins. The gels were cut into 10 mm slices, equilibrated for 40 minutes in SDS sample buffer (0.06M Tris-HCl pH 6.8, 2% SDS, 5% beta-mercaptoethanol, 10% glycerol), loaded onto the second dimension (10% SDS-PAGE), and run at 30 mA for 5 hours. This modified loading procedure increased the resolution of proteins in the second dimension gel electrophoresis. The gels were fixed and soaked in ENtensify (New England Nuclear, Boston, Mass.), dried, and autoradiographed with Kodak-X-AR film for 5 days.

6.1.14. SYNTHETIC PEPTIDES AND PURIFIED PROTEINS

Synthetic peptides NGRGDSLA, DESDET, and DDDDDD were constructed by the Synthetic Peptide Facility at Children's Hospital, Boston, Mass. Rat fibronectin was obtained from CalBiochem. Gelatin (type IV) was from Sigma (St. Louis, Mo.).

6.1.15. PRODUCTION OF ANTIBODIES

Rabbits were immunized with conjugates composed of the relevant synthetic peptide conjugated to keyhole limpet hemocyanin (KLH) in complete Freund's adjuvant, boosted in incomplete Freund's adjuvant four weeks later, and bled on days 35 and 42. The IgG fraction was obtained by twice applying the rabbit serum to a goat anti-rabbit IgG sepharose 4B column, washing the column with 0.15M NaCl and 0.5% glacial acetic acid, and collecting fractions in tubes containing 1M Tris (pH 8.0) for neutralization.

The IgG fraction of a rabbit antisera (termed "R-anti-RGD") raised against a synthetic peptide (NGRGDSL) representing a hydrophilic portion of the Ap-1 protein could precipitate the Ap-1 protein present in COS-A− supernatant.

6.1.16. MAST CELLS

Mouse mast cell populations were isolated and grown in vitro as previously described (Nabel, G., et al., 1981, Nature (London) 291:332–334; Galli, S. J., et al., 1982, J. Cell. Biol. 95:435–447) WBB6F$_1$-+/+ mast cells were derived from femoral bone marrow cells of adult (8 to 12 week old) WBB6F$_1$-+/+ mice (The Jackson Laboratory, Bar Harbor, Me.). The survival and growth of this mast cell population is strictly dependent on growth factor-containing conditioned medium (reviewed in Galli, S. J., 1987, Fed. Proc. 46:1906–1914). The cells were used for experiments 4 to 8 weeks after the initiation of in vitro culture, when the population contained greater than 95% mast cells by staining with Toluidine blue (Galli, S. J., et al., 1982, J. Cell. Biol. 95:435–447). Cl.MC/tlC9 is a cloned, growth factor-independent mast cell line which arose spontaneously from Cl.MC/9C9, a growth factor-dependent line derived from adult BALB/c mouse spleen cells, by limiting dilution and micromanipulation (Galli, S. J., et al., 1985, Cell. Immunol. 96:223–230). Cl.MC/C57.1, is a growth factor-dependent mast cell clone derived from adult C5BL/6J mouse bone marrow cells. Both Cl.MC/tlC9 and CL.MC/C57.1 are homogeneous mast cell populations which grow with a doubling time of 20 to 48 hours. The cells were washed three times with Dulbecco's Minimal Essential Medium (DMEM, GIBCO) without serum additives immediately before use in studies of Ap-1 binding.

6.1.17. MACROPHAGE CONTENT IN PERITONEAL CELLS

Cells from the peritoneal cavity of C57BL/6 mice were obtained by lavage following intraperitoneal injection of 5 ml PBS. The cells were washed twice with PBS before a 6 hour incubation in 6 well tissue culture plates (Costar, Cambridge, Mass.), or on coverslips in 60 mm dishes (for immunofluorescence, at $5 \times 10^6$ cells/ml in 1 ml Dulbecco's Minimal Essential Medium (DMEM)+ 0.5% bovine serum albumin (BSA) (Collaborative Research, Waltham, Mass.), at 37° C. After removal of nonadherent cells (approximately 50%) by washing three times with DMEM containing 0.5% BSA, the adherent cell population consisted of about 99% macrophages according to Giemsa and peroxidase staining (Thorens et al., 1987, Cell 48:671–679); no Thy1+ cells were detectable by immunofluorescence, and about 98% of the cells were murine Mac-3+ (as assayed by binding of anti-Mac-3 monoclonal antibody, Boehringer Mannheim, Indianapolis, Ind.). For assays of surface Ia expression (see Section 6.1.19 and subsections, infra), the adherent fraction was incubated an additional 96 hours in DMEM containing 5% FCS (Sigma, St. Louis, Mo.). No Ia+ cells were detectable at this time. The cells were then washed three times and incubated with MEM, 0.5% BSA supplemented with COS-A+ or COS-A− supernatants, or proteins such as rat gamma-interferon (Amgen, Thousand Oaks, Calif.; specific activity of approximately $10^7$ U/mg protein) or fibronectin.

6 1.18. BINDING OF LABELLED AP-1 TO CELLS

Binding of labelled Ap-1 to cells was performed according to Rao et al. (1983, Cell 36:889–895). Briefly, $10^5$ cells in DMEM+2% BSA (binding media) were incubated with various concentrations of $^{14}C$ or $^{35}S$ internally labelled COS-A+ or COS-A− supernatant for 25 minutes at room temperature. After three washes with 1 ml of binding media, the cells were layered in a final volume of 30 ul, over 100 ul of a mixture of 75% Dow Corning 550 fluid, 25% Fisher light paraffin oil, and centrifuged for 10 minutes at 4° C. at 1000 rpm in an Eppendorf centrifuge. The tip of the Eppendorf tube containing the pelleted cells was excised with a razor blade, and radioactivity was counted by liquid scintillation.

6.1.19. EXPRESSION OF Ia BY MACROPHAGES

Expression of Ia by macrophages was assayed by two methods: indirect immunofluorescence and FACS analysis.

6.1.19.1. ASSAY BY INDIRECT IMMUNOFLUORESCENCE

Peritoneal cells were obtained as described supra (Section 6.1.17) and washed twice before placing $10^4$ to $10^5$ cells per 22 mm round cover slip (VWR, Cambridge, Mass.) in 60 mm culture dishes (3 cover slips/dish). After removal of non-adherent cells by washing three times with MEM medium, 5% BSA, the adherent cells were incubated an additional four days in 5 ml DMEM+10% FCS alone, or after coating with gelatin (Type IV, Sigma). The coverslips were subjected to vigorous pipetting with MEM, 0.5% BSA before addition of 0.1 ml unlabeled COS-A+ supernatant, COS-A− supernatant, or 500 ug of fibronectin followed by incubation for an additional 0.5 to 12 hours in 5 ml MEM, 0.5% BSA.

To detect Ia, a rat monoclonal antibody, M5-114 (Boehringer Mannheim) that reacts with several murine Ia determinants, including Ia d,b,k was added (at 1:100 dilution as supplied by the manufacturer) to cells on cover slips. The cells were then incubated for 20 minutes at 4° C. and an additional 20 minutes at 37° C. After thoroughly washing the cover slips in PBS for 1 minute, rhodamine-labeled goat anti-rat IgG (Cooper Biomedical, Worcester, Mass.) (1:500 dilution in PBS) was added. The cover slips were then incubated for 30 minutes at 4° C., and were washed as above.

6.1.19.2. FACS ANALYSIS OF IA EXPRESSION BY MACROPHAGES

Cells: Resident peritoneal macrophages were isolated by obtaining cells from the peritoneal cavity of C3H/HcJ or C57bl/6 mice by lavage and aspiration with 6 ml PBS. $5 \times 10^5$ cells/ml were added to wells (Costar), or to round coverslips (VWR), and incubated at 37° C., 5% $CO_2$, in DMEM+10% fetal bovine serum (FBS)+100 units penicillin/streptomycin (Medium). This medium was also used to remove non-adherent cells. Adherent cells after 2 hours, 24 hours, or 7 days of incubation, were characterized as 95-99% macrophages by histochemical analysis using peroxidase, alpha-naphthyl esterase, Wright-Giemsa stain, and flow cytometry.

Cells from the WEHI-3 macrophage cell line (Cooper, P.C., et al., 1982, Leuk. Res. 6:313), and cells from the R8205 B cell line (Polla, B., et al., 1986, Proc. Natl. Acad. Sci. U.S.A. 83:4878-4882) were incubated at a final concentration of $5 \times 10$ cells/ml in 6-well tissue culture plates (Costar).

Surface Ia expression was determined using a hybridoma derived rat anti-mouse Ia (M5-114) monoclonal antibody (Boehringer Mannheim) containing 0.2 mg antibody/ml at a final dilution of 1:20 in DMEM containing 0.5% BSA. As a negative control, rat monoclonal anti Ly-2.1 antibody (56-6.7; Becton Dickinson, Mountain View, Calif.) (0.25 mg antibody/ml) was used. Following incubation with either M5-114 or 56-6.7 monoclonal antibody for 20 minutes, at 4° C. in 1×PBS containing 2% FCS, the cells were washed once in 1×PBS, and then incubated for 40 minutes at 4° C. with a fluorescein-labelled rat IgG (Cappel, West Chester, Penna.) (21.5 mg/ml of antibody at a final concentration of 1:100). After washing three times, the intensity of cellular immunofluorescence was measured using a fluorescence activated cell sorter (FACS).

6.1.20. INDIRECT IMMUNOFLUORESCENT DETECTION OF AP-1

Cells on cover slips, prepared as described in Section 6.1.19.1, were incubated with the IgG fraction of a rabbit antisera raised against either the synthetic peptide NGRGDSLA ("anti-G") or SDESDET (anti-S) subsequences of Ap-1. Antibody was added at 1:200 serum dilution in PBS, at 4° C. for 40 minutes, and washed twice before addition of fluorescein-conjugated goat anti-rabbit IgG (at 1:100 dilution in PBS, as supplied by Cooper Biomedical). In some cases, cells were fixed in DMEM containing 2% paraformaldehyde and 2% FCS for 1 to 2 minutes, and washed 5 times before microscopic analysis. Every cell in 10 to 25 random fields on each of the three coverslips/dish was visualized at 100× magnification, using a fluorescent photomicroscope (Olympus IMT2) with barrier filters of 420-490 nm for fluorescein, and 500-590 nm for rhodamine. The numbers of positive cells/field were assessed three times by two different observers.

6.1.21. MACROPHAGE CHEMOTAXIS ASSAY

6.1.21.1. DISH ASSAY $4 \times 10^5$ cells were placed at four equidistant points at the circumference of 60 mm dishes which were either uncoated or pre-coated with gelatin type IV. After 24 hours in MEM containing 0.5% BSA, non-adherent cells were removed by vigorous pipetting, leaving a cell population as described supra in Section 6.1.17. Fifty ul of Sepharose 4B beads that had been incubated with 0.5 ml of COS-A+ supernatant, 0.5 ml COS-A- supernatant, or 0.5 ml fibronectin (1.6 mg/ml), overnight at a pH of 7.0, was placed in a 15 mm well pre-coated with sterile silicon grease (Dow-Corning) in the center of 60 mm dishes, and covered with a thin layer of grease. Two ml MEM with 0.5% BSA was added to the dishes before incubation at 37° C. At 30 minutes, 1 hour, 3 hours, 6 hours, and 24 hours, 2 ml of 70% ethanol was added. After one minute, the cells were sequentially washed with PBS and $H_2O$. One ml of 2% Giemsa stain was added, and after 1 minute, the cells were immersed in water for 2 minutes. The numbers of cells in each of the following groups were then determined:

Group I: Perimeter (0-5 mm from dish circumference)

Group II: 5-15 mm from dish circumference

Group III: 15-20 mm from dish circumference.

The distance from the circumference of 50% of the cells in each dish was determined and expressed as the mean migration index.

6.1.21.2. MODIFIED BOYDEN CHAMBER ASSAY

Macrophage chemotaxis was also measured by a modified Boyden chamber assay.

The following agents were tested for chemotactic activity: N-formyl methionyl phenylalanine (FMLP; Sigma Chemicals, St. Louis, Mo.), COS-A+ supernatant, COS-A− supernatant, and 10% FBS (Sigma). Modified Boyden chambers (Neuroprobe, Calif.), separated by a micropore filter (polycarbonate, 13 mm diameter, 5 um pore size, Millipore, Mass.) were used to measure macrophage chemotaxis. Macrophages were obtained as described supra and placed onto the filter in the upper chamber at a concentration of $2 \times 10^6$ cells in 100 ul in DMEM containing 0.5% BSA. Cells were incubated at 37° C., 5% $CO_2$ (humidified) for 4 hours.

A checker board analysis of the chemattractant activity of AP-11 (Fx5) was performed by incubating different concentrations of this material in the upper and lower chambers in DMEM containing 1% BSA. After incubation, filters were sequentially fixed in 70, 90, and 100% ethanol (for 1 minute each) before staining with hematoxylin (Mayer's, pH 7.2) for 5–10 minutes. The number of macrophages adhering to the chemattractant side of the filter (i.e., cells that passed through the filter during the 4 hour incubation) were counted by inverse phase microscopy. All assays were performed in triplicate.

6.1.22. ASSAY OF MACROPHAGE TUMORICIDAL ACTIVITY

Resident peritoneal macrophages (RPM) and WEHI-3 cells, prepared in triplicate (in 24 well plates, Linbro) at a final concentration of $5 \times 10^5$ cells in 500 ul DMEM containing 0.1% BSA were incubated at 37° C., 5% $CO_2$ for 6 hours with Ap-1(Fx5), COS-A+ supernatant, COS-A− supernatant, or gamma-interferon, with $10^4$ $^{51}Cr$-labelled EL-4 cells (100 uCi sodium chromate-51 per $10^6$ EL-4 cells, labelled for 0.5 hour at 37° C.). Where indicated, RPM or WEHI-3 cells were incubated with different candidate macrophage activating factors for various time periods, and washed once before addition of $10^4$ $^{51}Cr$-labelled EL-4 cells followed by a six hour incubation. Maximum $^{51}Cr$ release was determined from $^{51}Cr$ cpm in supernatants of radiolabelled EL-4 cells after freeze-thawing three times. Spontaneous $^{51}Cr$ release represented radioactivity resulting from the incubation of cells with RPM or WEHI-3 cells, and DMEM containing 0.5% BSA. Specific lysis was calculated according to the following:

$$\text{Specific lysis} = \frac{100 (E - S)}{100 - S}$$

Where E=cpm released using COS-A+ or COS-A− supernatant
S=cpm from spontaneous lysis (measured using DMEM containing 0.5% BSA).

6.1.23. INDUCTION OF GRANULOCYTE/MONOCYTE COLONIES

Granulocyte and monocyte colonies (G/M colonies) were observed, following the in vitro incubation of $10^5$ cells/ml of bone marrow cells from 6 week old BALB/c mice. Cells were placed in 1 ml (RPMI 1640+10% fetal calf serum (FCS)+100 units penicillin/streptomycin and 3% Bacter Agar) in 30 mm dishes (Falcon 1008). Two or three identical plates were placed in a 100 mm petri dish. An additional plate containing only $H_2O$ was used to humidify the other dishes. The positive controls for induction of G/M colonies were dishes containing recombinant G/M CSF (5 U/ml).

Colony-stimulating activity was determined from the number of colonies formed after 7 days of incubation, where a colony was defined as greater than $10^2$ cells, and a cluster was defined as 10 to 50 cells. Cells were counted using an inverted phase Olympus microscope.

Groups for assessment of G/M colony-stimulating activity included:
1. COS-A+ supernatant (approximately 50 ng/ml culture medium)
2. COS-A-$^{31}$ supernatant (1 ml)
3. Gamma-interferon (100 U/ml culture medium)
4. DMEM
5. G/M CSF (200 U/ml culture medium)
6. G/M CSF (200 U/ml)+gamma-interferon (100 U/ml)
7. Gamma-interferon (100 U/ml)+COS-A+ supernatant (50 ng/ml)

6.1.24. SCREENING OF A HUMAN GENOMIC LIBRARY WITH THE MURINE AP-1 cDNA PROBE

A human genomic library was screened with the murine Ap-1 cDNA probe. The library, which was supplied to us, contains DNA equivalent to about 10 genomes, and was originally constructed by partial Sau3A-digestion of genomic DNA obtained from human liver, followed by insertion into the EMBL-3 (lambda phage derivative) vector.

The screening of the library was performed as described (Maniatis, T., et al., 1982, Molecular Cloning: A Laboratory Manual, Cold Spring Harbor Laboratory, New York). Filters (132 mm diameter, 0.45 um pore size) were prepared as described (id.) except that a higher phage density was used for plating ($5 \times 10^4$ to $1 \times 10^5$ pfu per dish). The filters were washed twice in 3X SSC/0.1% SDS at 65° C., prehybridized at 42° C. overnight (id., at pp. 320–323), and hybridized with $^{32}P$-labeled Ap-1 cDNA probe (id., at pp. 324–328. After several washes in solutions with different concentrations of SSC buffer with 0.1% SDS, the filters were exposed for autoradiography at −70° C. overnight. Plaques that hybridized to the Ap-1 probe were picked and placed into 1 ml of SM solution (id., at p. 70) containing a drop of chloroform, and stored at 4° C. overnight. The solutions were centrifuged for 3 minutes at 14,000 rpm in an Eppendorf microfuge, diluted 1:1000, and replated. After a 15 hour incubation, each plate contained 100–300 plaques. The plaques were transferred to nitrocelluose filters and rescreened with the Ap-1 probe as described above. DNA was extracted from phage in single positive plaques (Maniatis, T., et al., supra), digested with appropriate restriction enzymes, and analyzed by agarose gel electrophoresis (0.5% agarose, 1X TAE (Trisacetate EDTA buffer; Maniatis, T., et al., supra)). Southern blots were performed as previously described (Gatti, R. A. et al., 1984, Biotechniques 2:148–155).

6.2. ISOLATION OF A cDNA ENCODING AP-1

As described supra, a sublibrary was constructed which contained cDNA inserts that are selectively expressed by T cell subsets after activation by antigen or mitogen. The cDNA library ($3.8 \times 10^5$ independent clones) was constructed from an activated inducer T cell clone (Cl.Lyl-Tl), according to the procedure of Okayama and Berg (1983, Mol Cell Biol. 3:280–289). About $10^4$ colonies from this cDNA library were screened using a T cell cDNA probe from which B cell messages had been subtracted (T-B cDNA; see Section 6.1.5). After removal of colonies which hybridized with cDNA representing known lymphokines (e.g., IL-2, IL-3, gamma-interferon), analysis of the remaining colonies that were T cell specific showed that about 3% contained the same insert according to cDNA hybridization and restriction digestion analysis.

The XhoI fragment, containing all of the abundant (3%) cDNA insert, which was termed Ap-1 (activation protein-1), was used as a probe for Northern analysis, in order to detect any corresponding mRNA in different cell types (FIG. 1A). Steady-state levels of Ap-1 mRNA were very low or undetectable in unstimulated TH clones (FIG. 1A, lanes a, c), and increased substantially within 24 hours after activation by ConA (FIG. 1A, lanes b, d). The levels of poly(A)+ RNA in the natural killer (NK) T cell clone NK-11, also increased significantly after incubation with ConA (FIG. 1A, lanes e, f). By contrast, no hybridization was detected to poly(A)+ RNA from the mast cell clone MC-9 (Nabel, G., et al., 1981, Nature (London) 291:332–334) in the presence or absence of ConA (FIG. 1A, lanes g, h), from the murine B-cell tumor 2PK3 (FIG. 1A, lane i) or, using the hybridization conditions described, from PHA-stimulated human peripheral blood lymphocytes (PBL) (FIG. 1A, lane j). Further analysis showed that poly(A)+ RNA from unstimulated murine thymocytes and spleen cells also lacked detectable levels of Ap-1 message (FIG. 1B).

6.3. ISOLATION OF HUMAN GENOMIC AP-1 CLONES

Human genomic Ap-1 clones, with substantial homology to the murine Ap-1 cDNA sequence, have been obtained (FIGS. 1C, 1D) by screening a genomic library with the murine Ap-1 cDNA probe as described in Section 6.1.24, supra. The human genomic clone Hi92 contains a 17 kb insert. FIG. 1D reveals that the cloned human genomic fragment of Hi92 hybridizes with the (murine) Ap-1 cDNA probe.

6.4. STRUCTURE OF AP-1

The full-length XhoI fragment cDNA clone used as probe in the Northern analysis described supra was digested with various restriction enzymes to derive the restriction endonuclease pattern shown in FIG. 2A. The sequence of the cDNA clone (FIG. 2B) was determined by the method of Maxam and Gilbert (1980, Meth. Enzymol. 65:499–560). The sequenced cDNA of 1,569 bp contained an open reading frame (ORF) of 882 nucleotides (nucleotides number 268 to 1149) (FIGS. 2A, 2B), encoding a putative polypeptide with a predicted molecular weight of 32,462 daltons. The first methionine in this open reading frame (nucleotides number 223 to 225) fits the consensus for eukaryotic translation initiation signals (Kozak, M., 1984, Nucl. Acids. Res. 12:857–872). The 3'-noncoding sequence in the cDNA contains three potential polyadenylation signals (lower case letters in FIG. 2B) and lacks the consensus sequence "TTATTTAT" present in the mRNA encoding other defined T cell lymphokines (Caput, D., et al., 1986, Proc. Natl. Acad. Sci. U.S.A. 83:1670–1674).

The product of the open reading frame (ORF) in the sequenced Ap-1 cDNA is extremely hydrophilic (FIG. 3A), and displays several features of a secreted protein. One potential N-linked glycosylation site (N-X-S or N-X-T) is present at amino acids number 78–80, and there are 20 tripeptides with the sequence S-X-E and two tripeptides with the sequence S-X-P (FIG. 3A), that may serve as O-linked glycosylation sites (Oldberg, A., et al., 1986, Proc. Natl. Acad. Sci. U.S.A. 83:8819–8823) (FIG. 3). The ORF is unusually rich in aspartic and glutamic acid residues (22% D+E), and it has an isoelectric point (pI) of 4.18. A hydrophobic leader sequence is present which is similar to that of transferrin (Lucero, M. A., et al., 1986, Nucl. Acids Res. 14:8692). The leader sequence probably ends at the threonine residue at amino acid number 22 (FIG. 3A), since this position, immediately after the transition from the N-terminal hydrophobic sequence to a hydrophilic segment of the molecule, represents a suitable cleavage point for signal peptidases. Ap-1 lacks an obvious membrane-anchoring region (Sabatini, D. D., et al., 1982, J. Cell Biol. 92:1–19).

The tripeptide sequence arginine-glycine-aspartate (RGD) (FIGS. 2B, 3A) is present in Ap-1. The RGD-motif forms a critical part of the binding site to receptors on target cell populations of a family of extracellular proteins that are involved in cell migration and interaction (Ruoslahti, E. and Pierschbacher, M. D., 1986, Cell 44:517–518). The family includes fibronectin, fibrinogen, parvalbumin, thrombospondin, and vitronectin. The RGD tripeptide in Ap-1 is located at amino acid residue numbers 144–146, and is present within a longer subsequence that is highly homologous to that surrounding the RGD motif in fibronectin (FIG. 2C).

There are two hydrophilic stretches in Ap-1 (amino acid residues 85–96 and 200–207) that are similar to subsequences in thrombospondin that have been associated with calcium binding (Lawler, J. and Hynes, R. O., 1986, J. Cell. Biol. 103:1635–1648). These two subsequences are likely to constitute calcium binding sites since most, if not all, vertex positions are occupied by aspartic acid residues (Tufty, R. H. and Kretsinger, R. H., 1975, Science 187:167–169).

6.5. EXPRESSION OF AP-1 IN COS CELLS

Figures 4A, 4B:
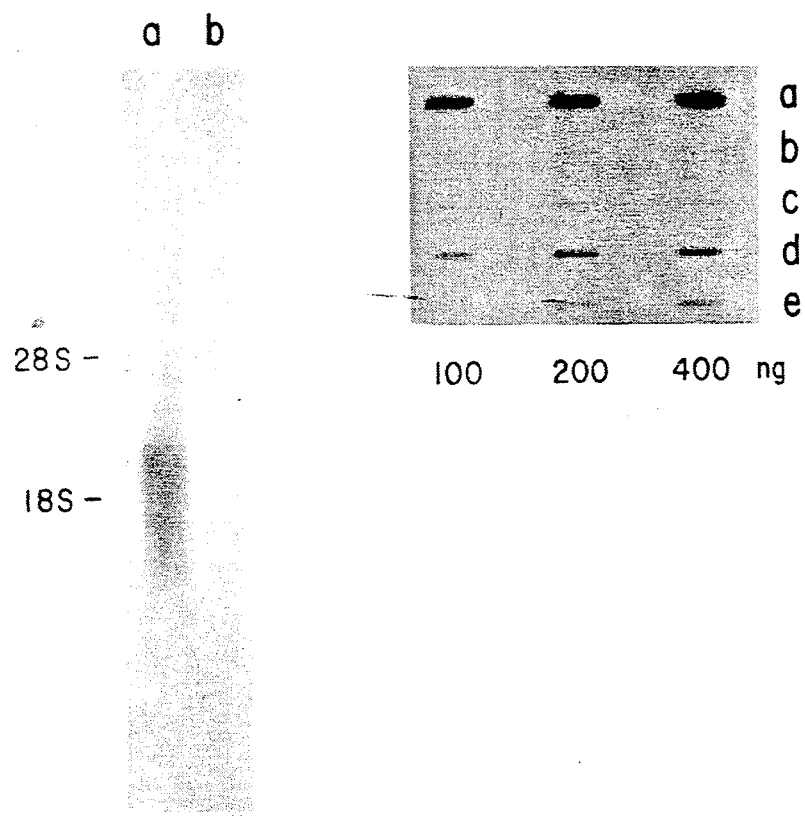

COS (monkey kidney) cells were transfected with a pCD vector containing a full-length Ap-1 cDNA insert, or transfected with a pCD vector lacking the cDNA insert. Poly(A)+ RNA from COS cells was obtained 72 hours after transfection and tested for Ap-1 transcription by Northern analysis using nick-translated Ap-1 cDNA as a probe (FIG. 4A). The probe hybridized with a 2.2 kb RNA from COS cells transfected with pCD-Ap-1 (lane a) that corresponds to the expected size message plus SV40 sequences. No hybridization was detectable in RNA from COS cells transfected with the (parental) pCD vector (lane b). Analysis of Ap-1 transcription at intervals after COS cell transfection showed that maximal steady state levels of Ap-1 RNA were present 72 hours after transfection (FIG. 4B). Further experiments have shown that cDNA transcription increases rapidly between 48 and 72 hours to maximal levels, and substantially decreases by 86 hours.

Supernatants from COS cells that had been transfected with pCD-Ap-1 were designated as COS-A+, and supernatants from pCD (mock) transfected COS cells were designated as COS-A−.

In order to determine the size of the fully glycosylated Ap-1 protein, $^{35}$S-methionine-labeled COS-A+ supernatant was subjected to the two-dimensional isoelectric focusing/electrophoretic analysis described in Section 6.1.12, supra. $^{35}$S-methionine labeling was carried out as described in Section 6.1.9, supra. The results of the two-dimensional gel separation are shown in FIG. 4C. The analysis of COS-A+ and COS-A− supernatants from labeled cells revealed identical protein patterns, except for a diffuse band corresponding to a molecular weight of approximately 60 kd and a pI of about 4.5 that was present in COS-A+ supernatant and absent from COS-A− supernatant fluids (FIG. 4C). Thus, the fully glycosylated Ap-1 protein produced by transfected COS cells has an apparent molecular weight of approximately 60 kd.

Additional experiments demonstrated that the carbohydrate moieties of Ap-1 include terminal sialic acid residues. Ap-1 was purified from COS-A+ supernatants by lectin affinity chromatography, by use of the horseshoe crab (*P. limulus*) lectin, which is specific for sialic acid. After elution with increasing salt and low acid conditions, only the approximately 32 kd core Ap-1 protein was recovered. Thus, Ap-1 was apparently bound through its terminal sialic acid residues, which were, however, cleaved off the protein under the conditions used for elution.

Since the Ap-1 protein lacks cysteine residues, its position on the polyacrylamide gel is not altered by cleavage of disulfide bonds. Expression of the Ap-1 cDNA in COS cells (monkey kidney cells) normally ensures correct glycosylation. There are 22 potential O-linked (Oldberg, A., et al., 1986, Proc. Natl. Acad. Sci. U.S.A. 83:8819-8823) and one N-linked glycosylation sites; the experiments described supra indicate that the 32 kd molecular weight core protein predicted from the cDNA sequence (FIG. 2B) may be glycosylated to an apparent molecular weight of approximately 60 kd.

6.6. PURIFICATION OF AP-1

Ap-1 protein was purified by DEAE-cellulose ion exchange chromatography as described in Section 6.1.12.

Fractions obtained after ion-exchange chromatography of 100 ml COS-A+ supernatant were tested for activation of RPM or cells from the WEHI-3 macrophage cell line. One fraction (fraction 5), containing a single protein species of approximately 60 kd and a pI of 4.5 according to migration in IEF gel electrophoresis (FIG. 5), induced tumoricidal activity. The 60 kd protein detected in fraction D was considered purified Ap-1 protein, as judged by the criteria of silver staining in SDS-polyacrylamide gels, and was termed Ap-1(FxD). The dose response curves for tumoricidal activity of COS-A+ supernatant and Ap-1(Fx5) were parallel, suggesting that ion exchange chromatography had not qualitatively changed the biological activity of Ap-1 in this assay (FIG. 12). The active fraction, Ap-1(Fx5), contained approximately $8 \times 10^3$ units of activity, suggesting that this fraction accounted for virtually all of the MAF activity in the COS-A+ supernatant. The amount of protein in Ap-1(Fx5), determined by spectrophotometric analysis (280 nm), was approximately 200 ug (FIG. 5), indicating approximately 20 ng of Ap-1 per unit of MAF.

6.7. ANALYSIS OF BIOLOGICALLY ACTIVE SUBSEQUENCES OF AP-1

There are several repeats in Ap-1 at both the nucleotide and protein sequence levels, shown in FIG. 3B. The following studies were intended to define subsequences responsible for binding activities and corresponding functions of the Ap-1 molecule.

6.7.1. AP-1 BINDING TO SUBSETS OF IMMUNOLOGICAL CELLS

Peritoneal macrophages, thymocytes, a mast cell clone, and a subset of resting and activated T cells bound to a significant portion (20–50%) of COS-A+ $^{14}$C-labeled supernatant (FIG. 6A). B cells, NIH3T3 cells, and L-929 cells bound less than 0.1% of input cpm after addition of approximately $1.5 \times 10^4$ TCA-precipitable cpm of COS-A+ supernatant. Virtually all of the cpm bound can be ascribed to Ap-1 binding, since binding activity in the COS-A+ supernatant was reduced greater than 95% (a) after precipitation with the IgG fraction of a rabbit antiserum raised to a hydrophilic subsequence of Ap-1 ("R anti-RGD") but not with normal rabbit IgG, or (b) in the presence of a 50 fold excess of unlabeled COS-A+ supernatant. The extremely low levels of non-specific binding noted in the analysis may be due to the fact that over 80% of the $^{14}$C-labeled protein represented Ap-1, which is extremely hydrophilic and may not exhibit significant levels of non-specific attachment to cells.

The observed binding of Ap-1 to certain cell types may reflect an interaction of the recombinant Ap-1 protein with a homogeneous set of surface binding sites or, alternatively, it may reflect interactions between the ligand and several different binding sites, perhaps distributed in a cell-type specific fashion.

6.7.2. CONTRIBUTION OF THE RGD-CONTAINING SUBSEQUENCE TO AP-1 ATTACHMENT

COS-A+ supernatant was added to cells from three independent mast cell populations. Over 50% of the cells from each population were positive by indirect immunofluorescence using a rabbit anti-RGD antibody. The Cl.MC-TIC9 cells, a cloned mast cell line, showed the same number of immunofluorescent cells after addition of 0.5, 0.1, or 0.01 ml of COS-A+ supernatant, while the other two mast cell lines tested, MC-C57 and MC+/+, displayed a linear decrease in the numbers of immunofluorescent cells (as well as in intensity of fluorescence) as the concentration of Ap-1 was reduced 50 fold (FIG. 6B). Binding was due to Ap-1 in COS-A+ supernatant, since precipitation of the supernatant with anti-RGD resulted in loss of binding activity, and COS-A+ supernatant proteins did not bind to the mast cell lines. These studies also showed that these mast cells lacked receptors for fibronectin-gelatin or vitronectin. Addition of an excess amount of different synthetic peptides representing Ap-1 subsequences showed that the RGD-containing subsequence (NGRGDSLA) of Ap-1 blocked binding of Ap-1 to cells, while the aspartate-rich subsequence (DDDDDDDD) (FIG. 6B) or a third subsequence (DESDET) did not block binding.

6.8. ANALYSIS OF BIOLOGICAL ACTIVITIES OF AP-1

6.8.1. Macrophage Chemotactic Activity

As described in Section 6.1.21.1, peritoneal cells from C57Bl/6 mice were added to the periphery of a 60 mm dish containing media plus or minus gelatin. After three hours of incubation, the non-adherent cells were removed, leaving a cell population that was greater than 98% peroxidase positive (i.e., macrophages). Sepharose 4B beads that had been incubated with COS-A+ supernatants, COS-A- supernatants, or fibronectin were added to a 15 mm well in the center of the 60 mm dish. Immunofluorescent staining at 0.5, 3, and 8 hours, showed that Ap-1 or fibronectin released into the dish was detectable at 0.5 hour after the beads were placed in the central wells, and that the concentration of the molecule in the dish was inversely proportional to the distance from the well. By 3 hours, the gradient had reached the periphery of the dishes.

Migration towards the center of dishes containing COS-A+ beads was noted within 0.5 hour. By 3 hours, 50% of the cells had migrated to the perimeter of the central well in both uncoated dishes and gelatin-coated dishes. At 24 hours, cells that had migrated to the edge of the central well showed morphological evidence of activation and ingestion of the Sepharose beads (FIG. 8). No detectable migration was noted in dishes containing COS-A-- beads or in dishes containing fibronectin beads, whether or not the dishes had been precoated with gelatin.

Peritoneal macrophages were also added to dishes containing Sepharose 4B beads preincubated with a mixture of Ap-1 and a 100 fold excess of either the RGD containing synthetic octamer peptide (NGRGDSLA) or two other synthetic peptides (an aspartate hexamer or DESDET) (FIG. 7). Migration of cells in dishes containing a mixture of Ap-1 and the RGD-containing octamer, but not the aspartate hexamer or DESDET, was inhibited by about 50% in two experiments (FIG. 7).

In further experiments, carried out as described in Sections 6.1.21.2, the ability of Ap-1 to induce directed migration of macrophages was tested by a modified Boyden chamber assay. The results are presented in Table I.

TABLE I

| MACROPHAGE CHEMOTACTIC ACTIVITY OF AP-1* | | | | | |
|---|---|---|---|---|---|
| | Upper chamber: Ap-1 Concentration (ug/ml) | | | | |
| | 0.001 | 0.004 | 0.01 | 0.4 | 4.0 |
| Lower Chamber: Ap-1 Concentration (ug/ml) 4.0 | 78 | 56 | 22 | 5 | 2 |
| 0.4 | 32 | 21 | 14 | 2 | 1 |
| 0.01 | 21 | 10 | 2 | 7 | 2 |
| 0.004 | 5 | 1 | 1 | 1 | 1 |
| 0.001 | 1 | 1 | 1 | 1 | 1 |

*Resident peritoneal macrophages ($2 \times 10^6$) were placed in the upper chamber of a Boyden apparatus. The numbers of cells ($\times 10^4$) that migrated toward the lower chamber are shown.

As shown in Table I, Ap1 induced the directed migration of macrophages. Macrophage migration across filter chambers separating the upper and lower chambers varied directly with the size of the concentration gradient of Ap-1 (Table I). Moreover, since cell migration from one chamber to the other was not detected when the two chambers contained high but equal concentrations of Ap-1, cell movement across the membrane did not reflect gradient-independent excitation of cell motility ("chemokinesis"). Comparison of cell migration across Ap-1 gradients to migration across gradients formed by the bacterial peptide FMLP (a known mediator of macrophage chemotaxis; Schiffman, E., et al., 1978, in Leukocyte Chemotaxis, Gallin, J. I. and Quie, P. G., eds., Raven Press, New York) indicated similar levels of chemattractant activity (Table I).

6.8.2. MACROPHAGE ACTIVATION: Ia INDUCTION

6.8.2.1. Assay By Indirect Immunofluorescence

Since macrophages that had migrated across an Ap-1 gradient revealed morphological changes consistent with activation (FIG. 8), we asked whether attachment of Ap-1 to Ia macrophages (after 5 days in vitro culture) resulted in expression of Ia molecules at the cell surface.

Rabbit antibody to synthetic peptides from Ap-1 and a monoclonal rat antibody to the murine Ia molecule were used for dual fluorescent analysis of the cells. After addition of Ap-1 and incubation for 30 minutes at 4° C., anti-Ap-1 immunofluorescence showed that about 95% of the cells in the COS-A+ dishes displayed immunofluorescent "halos". 60% of these cells showed bright red patches within the green halo after rhodamine-staining using a monoclonal Ia antibody at 4° C. (FIG. 9). The addition of gelatin to the dishes had no effect on the number of cells positive for Ap-1 or Ia. About 5% of cells in the dishes containing COS-A- supernatant were weakly positive for either Ap-1 or Ia.

Analysis of cells from dishes containing fibronectin and gelatin showed that about 95% had bound fibronectin according to immunofluorescence. Less than 5% reacted (weakly) with Ia antibody. Fibronectin does not occupy the macrophage Ap-1 binding site(s), since 100 fold excess of soluble fibronectin in the presence or absence of a gelatin matrix had no effect on binding of Ap-1 to macrophages. Incubation of cells with a mixture of COS-A+ supernatant (containing about 1 ug according to immunoprecipitation) and a 100 fold excess of fibronectin (200 ug) on gelatin-coated plates had no detectable effect on Ap-1 binding as judged by immunofluorescence. Moreover, an excess of Ap-1 did not inhibit fibronectin binding to macrophages. Incubation of cells on gelatin-coated plates with 1 ug of fibronectin and 100 fold excess of Ap-1 had no effect on fibronectin binding as judged by immunofluorescence.

It is not likely that Ia-induction involved production of gamma-interferon by contaminant T cells, for the following reasons: (i) virtually all adherent cells were positive for Mac-1, a marker that distinguishes macrophages from lymphocytes, and (ii) expression of Ia was apparent within 30 minutes after addition of Ap-1, which is consistent with a direct effect of the recombinant protein on the target macrophages.

6.8.2.2. FACS ANALYSIS

The ability of purified Ap-1 to induce Ia expression on macrophages was demonstrated by FACS analysis. FACS analysis was carried out as described in Section 6.1.19.2, supra, for resident peritoneal macrophages (RPM) treated with COS-A+ supernatant, gamma-interferon, or COS-A- supernatant (FIG. 10A). The results showed that both Ap-1 (in COS-A+ supernatant) and gamma-interferon induced substantial Ia expression, while COS-A- supernatant had no such effect. In further experiments, Ap-1(FxD) was also demonstrated to induce Ia expression on RPM.

To rule out the possibility that the induction of Ia expression by Ap-1 was caused by Ap-1-induced activation of a T cell population to produce gamma-interferon, thereby inducing the observed Ia expression, the experiment of FIG. 10A was repeated using a macrophage cell line. The macrophage cell line WEHI-3 was employed to ensure the absence of contaminating T cells. An analysis of Ia expression on WEHI-3 macrophage cells after incubation with COS-A+ supernatant, gamma-interferon, or COS-A− supernatant is shown in FIG. 10B. The results demonstrated that Ap-1 (in COS-A+ supernatant) or gamma-interferon could induce substantial Ia expression on this macrophage cell line, while COS-A− supernatant had no such effect. The induction of Ia expression by Ap-1 in the absence of contaminating T cells demonstrated that the induction was not an indirect result of Ap-1-induced activation of T cells.

Ap-1(in COS-A+ supernatant) and BSF-1 (B cell stimulating factor, B cell growth factor, IL-4) were also tested for their ability to induce Ia expression on a murine B cell line, R8205. As shown in FIG. 10C, BSF, but not Ap-1, was able to induce B cell Ia expression. Like gamma-interferon, Ap-1 can selectively induce Ia expression on macrophages, but not B cells.

6.8.3. MACROPHAGE ACTIVATION: PHAGOCYTOSIS

The ability of Ap-1 to induce peritoneal macrophages to express phagocytic activity was tested at intervals after the addition of latex particles, in cultures supplemented with 0.5% BSA and either COS-A+ or COS-A− supernatants (0.1 ml). Within 5 hours, over 90% of macrophages in the cultures with COS-A+ supernatant, and less than 2% in the cultures with COS-A− supernatant, expressed phagocytic activity (Table II). Ingestion of latex beads did not require the continuous presence of COS-A+ supernatant, since macrophages that had been washed after incubation with COS-A+ supernatant, before latex bead addition, acquired phagocytic activity (Table II).

TABLE II

THE ABILITY OF AP-1 TO INDUCE
PHAGOCYTIC ACTIVITY IN MACROPHAGES*

| Group | Supernatant Added to Cultures | Incubation (minutes) | Latex Ingestion (%) |
|---|---|---|---|
| I | NONE | 90 | 1.1 |
|   |      | 150 | 1.7 |
|   |      | 240 | 1.7 |
| II | COS-A− | 90 | 0 |
|    |        | 150 | 0 |
|    |        | 240 | 0 |
| III | COS-A− | 90 | 70.0 |
|     |        | 150 | 87.0 |
|     |        | 240 | 94.1 |
| IV | **COS-A+ | 240 | ***98.4 |

*Dishes containing $10^5$ peritoneal macrophages were incubated in MEM, 0.5% BSA, with $10^8$ latex beads (1 micrometer diameter) and 0.1 ml of the indicated supernatants. Cells ingesting more than 5 beads were scored as positive after microscopic observation of 20–30 random fields (approximately 300–500 cells/dish).
**0.1 ml COS-A+ supernatant was incubated with macrophage cultures for two hours. After washing cells 3 times with MEM + 0.5% BSA, latex beads were added and the numbers of cells that had ingested more than 5 beads were scored at the indicated times.
***Unlike group III, where the majority of cells that had contained injested latex beads also had surface-associated beads ("rosettes"), group IV cells showed ingestion of beads but no rosettes.

6.8.4. MACROPHAGE ACTIVATION: INDUCTION OF CYTOTOXICITY

Tumoricidal activity in COS-A+ supernatant fluids was quantitated by addition of 10-fold dilutions of this material to resident peritoneal macrophages (RPM) ($10^5$ cells) and $10^4$ $^{51}$Cr-labelled EL-4 cells. Macrophage lysis of tumor cells was directly proportional to the concentration of COS-A+ supernatant fluid present during the 6 hour incubation period (FIG. 11). Units of activity in COS-A+ and COS-A− supernatant fluids were quantitated according to final concentrations necessary to induce macrophages to lyse 33% of $^{51}$Cr-labelled tumor cells. The calculated results indicated no detectable activity in COS- A− supernatant fluids, while COS-A+ supernatant fluids contained approximately $10^4$ units/10 ml COS-A+ supernatant (FIG. 11).

Ap-1 purified by ion-exchange chromatography was also tested for cytotoxic activity against tumor cells. The results, shown in FIG. 12, demonstrated that Ap-1(FxD) had significant tumoricidal activity. The dose response curves for tumoricidal activity of COS-A+ supernatant and Ap-1(Fx5) were parallel, indicating that the activity was not qualitatively changed. Ap-1(Fx5) contained approximately $8 \times 10^3$ units of activity, which suggested that this purified sample accounted for virtually all the MAF activity in the COS-A+ supernatant.

By contrast, RPM or WEHI-3 cells incubated for 18 hours with gamma-interferon at concentrations as high as 4000 U (1 ug/ml) did not express significant cytotoxic activity within 12–24 hours. Analysis of the time course of macrophage activation by Ap-1(Fx5) indicated that macrophages expressed substantial tumoricidal activity within 3 hours of incubation. In contrast, mixtures of gamma-interferon (1000 U) and LPS (1 ug/ml) did not induce substantial levels of macrophage cytotoxicity until 24 to 36 hours (FIG. 13). Although gamma-interferon alone did not activate macrophages to express tumoricidal activity, we tested the hypothesis that gamma-interferon might influence the MAF activity mediated by Ap-1. RPM cells incubated with a mixture of 100 ng Ap-1+100 ng gamma-interferon (1000 U) showed a pronounced inhibition of tumoricidal activity (FIG. 13) relative to that induced by Ap-1 alone.

We have observed that the addition of normal cells as targets for lysis, in lieu of tumor cells, yields no significant induction by Ap-1 of cell lysis; thus, the induction of macrophage cytotoxicity mediated by Ap-1 appears to involve both specific recognition of and lytic activity toward "abnormal" (e.g., tumor) cells.

6.8.5. INDUCTION OF GRANULOCYTE/MONOCYTE PROGENITOR CELL DIFFERENTIATION

Ap-1 (COS-A+ supernatant) was tested for its ability to induce differentiation of granulocyte/monocyte progenitor cells, by the in vitro granulocyte/monocyte colony forming unit (GM-CFU) assay described in Section 6.1.23. The results are shown in Table III.

TABLE III

INDUCTION OF GRANULOCYTE/MONOCYTE
PROGENITOR CELL DIFFERENTIATION BY AP-1

| Experimental Group | Test Material | No. of G/M*** Colonies/mm²* Exp. 1 | Exp. 2 | No. of G/M*** Clusters/mm²** Exp. 1 | Exp. 2 |
|---|---|---|---|---|---|
| A. | COS-A+ | 122 | 94 | 56 | 45 |

TABLE III-continued

INDUCTION OF GRANULOCYTE/MONOCYTE
PROGENITOR CELL DIFFERENTIATION BY AP-1

| Experimental Group | Test Material | No. of G/M*** Colonies/mm²* Exp. 1 | Exp. 2 | No. of G/M*** Clusters/mm²** Exp. 1 | Exp. 2 |
|---|---|---|---|---|---|
| | supernatant (Ap-1) | | | | |
| B. | G/M CSF | 115 | 89 | 24 | 19 |
| C. | G/M CSF + gamma-interferon | 13 | ND | 0 | ND |
| D. | Gamma-interferon + Ap-1 (1:1) | 18 | ND | 5 | ND |
| E. | COS-A⁻ | 4 | 5 | 0 | 0 |
| F. | DMEM (control medium) | 5 | 4 | 0 | 0 |
| G. | Gamma-interferon | 5 | 11 | 0 | 0 |

ND: Not done
*Colony defined as greater than $10^2$ cells
**Cluster defined as 10-50 cells
***G/M: Granulocyte/Monocyte As shown in Table III, Ap-1 (Exp. Group A) induced bone marrow progenitor cells to give rise to granulocyte/monocyte clusters and colonies, at a level similar to that of G/M CSF (Exp. Group B). By contrast gamma-interferon (Exp. Group G) had no detectable colony (or cluster)-stimulating activity alone, and appeared to inhibit the colony/cluster-stimulating activities of Ap-1 (in Exp. Group D) and of G/M-CSF (in Exp. Group C). Analysis of the colonies induced by Ap-1 revealed that over 90% were composed of pure macrophages, while GM-CSF induced colonies that were 60% mixed granulocyte-monocyte, 15% pure granulocytes, and only 25% pure macrophages.

6.9 EXPRESSION OF AP-1 IN AUTOIMMUNE MICE

The experimental results described herein demonstrate that the lymphoid cells of mice which have a specific autoimmune disorder express Ap-1 at increased levels relative to normal mice.

MRL-lpr/lpr, but not MRL +/+, mice have been termed "lupus" mice because they spontaneously develop an autoimmune disorder resulting in lymphadenopathy arteritis, chronic proliferative glomerulonephritis, and arthritis (Theofilopoulos, A. N. and Dixon, F. J., 1985, Advances in Immunol. 37:269-392; Kelley, V. E. and Roths, J. B., 1985, Clin. Immunol. Immunop. 37:220-229; Kelley, V. E. and Roths, J. B., 1982, J. Immunol. 129(3):923-925). The onset and progression of this disorder is coincident with the appearance of large numbers of activated macrophages in the spleen and peritoneal cavity (Kelley, V. E. and Roths, J. B., 1985, Clin. Immunol. Immunop. 37:220-229; Kelley, V. E. and Roths, J. B., 1982, J. Immunol. 129(3):923-925).

Since the genetic basis of this disorder is carried by lymphoid cells (Theofilopoulos, A. N. and Dixon, F. J., 1985, Advances in Immunol. 37:269-392), we asked whether Ap-1 cDNA defined a gene that might be abnormally expressed in the lymphoid cells of MRL-lpr animals at progressive stages of this disease. RNA was extracted from thymus, spleen, and lymph node (LN) cells of MRL-lpr mice either before or after appearance of lymphoid hyperplasia and activated macrophages. Quantitative slot blot analysis of RNA from lymph nodes or spleen from MRL lpr/lpr animals which expressed the disease revealed a marked increase of Ap-1 RNA levels compared with disease-free MRL-lpr/lpr or MRL +/+ animals. Ap-1 cDNA hybridized to RNA from thymus of MRL-lpr/lpr mice both before and after the onset of disease (FIG. 11).

6.10 DISCUSSION OF THE BIOLOGICAL ACTIVITIES OF AP-1

After a lymphocyte recognizes antigen on the surface of a somatic cell or on an "antigen-presenting" cell, an efficient inflammatory response depends on attraction and activation of immunological cells to the site of recognition. Ap-1 secretion by activated lymphocytes may represent the molecular basis of effector cell recruitment and activation. Ap-1 is rapidly and abundantly transcribed and secreted after activation of T lymphocyte and Thy1+ NK cell clones, but not mast cell clones, resting spleen cells, thymocytes (FIG. 1), or fibroblasts. We have demonstrated the production of Ap-1 by lymphocyte clones grown in long-term culture. Preliminary experiments indicate that T cells directly explanted from murine spleen also produce Ap-1, twelve hours after stimulation with MHC-incompatible cells.

The recombinant Ap-1 molecule is released into the supernatant after expression of the cDNA in COS cells. This secretion is consistent with its molecular structure, which contains an N-terminal leader sequence and lacks a hydrophobic membrane anchor (FIG. 3). Two dimensional electrophoresis revealed a 60 kd moiety, representing approximately 5% of the total internally-labelled protein in supernatant fluid of COS-A+ cells (FIG. 4C). Since expression in COS cells normally ensures correct glycosylation, the weight and size of the protein may reflect the contribution of carbohydrates attached to an N-glycosylation site (amino acid residues 78-80) and/or 22 potential O-glycosylation sites.

After ion-exchange chromatography of COS-A+ supernatant, a fraction was identified that activated macrophages, as indicated by acquisition of tumoricidal activity. SDS-PAGE analysis of this fraction revealed a single band migrating at approximately 60 kd. Exposure of macrophages to Ap-1 in the absence of serum, LPS, or endotoxin, resulted in expression of tumoricidal activity with kinetics similar to those displayed by macrophage activating factors (MAF) (6-12 hours), and more quickly than that induced by gamma-interferon (which requires at least 48 hours in culture). A dose response analysis of Ap-1 was consistent with direct activation of resident peritoneal macrophages or the macrophage line WEHI-3 by nanogram amounts of Ap-1 (FIG. 8).

In addition to macrophage activation, as judged by acquisition of tumoricidal activity and surface Ia, interaction between recombinant Ap-1 and macrophages resulted in directed migration across a gradient of the recombinant protein (Table I). The hydrophilicity of Ap-1 (FIG. 3) may facilitate formation of a gradient after its release from activated T cells, by decreasing non-specific (hydrophobic) binding to molecules or cells lacking Ap-1 receptors. Inspection of monocytes approaching the source of Ap-1 release showed they had ingested Sepharose 4B beads (FIG. 8), and Ap-1-induced phagocytic activity was directly confirmed using latex beads. Thus, Ap-1 production by activated T cells or Thy1+ NK cells presumably serves to attract and activate macrophage phagocytic activity. In contrast, gamma-interferon released by activated T cells appears to prevent LPS and Fc receptor-mediated phagocytosis (Thorens, B., et al., 1987, Cell 48:671-679), and gamma-interferon gradients do not stimulate macrophage migration. Induction of macrophage activity by recombinant Ap-1 is masked in the presence of recombinant gamma-interferon (FIG. 9). It is unlikely that gamma-interferon directly blocks specific binding of Ap-1 to macrophages, since inhibition was observed with mixtures of equimolar amounts of the two recombinant proteins.

The observation that internally-labelled Ap-1 binds to peritoneal macrophages and T cells but not to B cells (or fibroblasts) suggests that target cells for this gene product are directly involved in induction of cell-mediated immunity. Since Ap-1 binds to a subset of resting peripheral T cells and thymocytes (FIG. 5), Ap-1 may mediate cellular interactions between activated T cells and resting or immature T cells. Activated T cells could influence mast cell function at sites of cell-mediated immunity through the binding of Ap-1 to mast cells.

Inspection of the primary structure of Ap-1 indicates that its ability to induce phagocytosis does not depend on the generation, through proteolytic cleavage, of a TKPR tetrapeptide ("tuftsin"), which also stimulates phagocytosis after proteolysis of the Fc region of IgG complexed to the Clq component (Najjar, V. A., 1974, Adv. Enzymol. 41:129-178).

A synthetic peptide containing the RGD subsequence inhibited Ap-1 binding and Ap-1-induced cell migration. Binding of the RGD motif in Ap-1 to its receptor may be mediated through the reverse sequence (DGR). Charge complementarity between RGD and the reversed sequence (DGR), where the positive charge of arginine is paired with the negative charge of aspartate at two sites, may contribute to binding. Along with charge complementarity, there may be a second component of binding reflecting a requirement for precise fit between the side chains of the RGD amino acids and its substrate.

There is good evidence that a critical step in passage of lymphocytes from the blood stream is binding of these cells to a receptor on small venules (Gallatin, M., et al., 1986, Cell 44:673-680). Recent definition of this receptor shows that it includes a ubiquitin chain that bears a reversed RGD-subsequence (DGR) (Siegleman, M., et al., 1986, Science 231:823-829). If the amino acids surrounding the DGR subsequence determine a specific configuration for binding to the RGD tripeptide in Ap-1, cells carrying Ap-1 molecules would be equipped to interact with the homing receptor and thus pass out of the blood stream.

Ap-1 may carry cellular binding sites that allow selective interactions with different cell types. In fibronectin, an additional cellular binding site similar to RGD (RED) has been reported (Humphries, M. J., et al., 1986, J. Cell Biol. 103:2637-2647), and a subsequence (CDPGYIGSR) lacking the RGD tripeptide is likely to contribute to cell attachment of the laminin protein, but is not present in either fibronectin or Ap-1 (Graf, J., et al., 1987, Cell 48:989-996). Structural features of Ap-1 other than the direct sites of interaction may influence its ability to bind to cells and induce new functions. Although Ap-1 does not display phosphorylation sites similar to those present in glycogen synthetase, pyruvic dehydrogenase and myosin light chain (reviewed by Krebs, E. G. and Beavo, J. A., 1979, Ann. Rev. Biochem. 48:923-959), it is rich in serine residues (17% S). Four contiguous serine residues at the carboxyl end of the molecule could be potential phosphorylation sites. Moreover, the serine in the RGDS subsequence may also be phosphorylated. A similar subsequence, REDS, is phosphorylated in bovine fibronectin (Petersen, T. E., et al., 1983, Proc. Natl. Acad. Sci. U.S.A. 80:137-141).

Preliminary experiments indicate that Ap-1 may bind to a series of transformed cell lines, but not to their normal counterparts, via an alternative attachment site (KED). It is possible that macrophages and transformed cells contain potential RGD receptors but can inactivate the RGDS ligand by selective phosphorylation of the 3' adjacent serine, leaving an alternative site as the major attachment sequence. Supporting this view are reports indicating the existence of cell surface protein kinase activity (Kubler, D., et al., 1982, J. Biol. Chem. 257:322-329; Kubler, D., et al., 1983, Proc. Natl. Acad. Sci. U.S.A. 80(13):4021-4025), and findings that transformed cells phosphorylate fibronectin substantially more efficiently than normal cells (Ali, I. U. and Hunter, T., 1981, J. Biol. Chem. 256(14):7671-7677). In principle, phosphorylated Ap-1 residues could also be involved in glypiation, but this possibility may be less likely, since Ap-1 lacks a hydrophobic tail which is normally removed for attachment of a glycolipid according to studies of proteins that undergo this phenomenon (reviewed by Cross, G. A. M., 1987, Cell 48:179-181).

A search of the PIR/NBRF protein sequence database, using the Intelligenetics program IFIND for proteins homologous (greater than 90%) to Ap-1, revealed that Ap-1 is highly homologous to the rat bone sialoglycoprotein, termed osteopontin, isolated from sarcoma cells. The 5' non-coding regions in the cDNAs of rat osteopontin and mouse Ap-1 differ significantly, while their 3'-noncoding regions are very similar. There are three potential polyadenylation signals present in the 3' non-coding regions of both the Ap-1 and osteopontin genes. Two of these signals have been shown to be functional in osteopontin. It is likely that these two potential polyadenylation signals are also functional in the Ap-1 messenger. Osteopontin contains two additional repeats of a subsequence that is present only once in Ap-1. In addition, although Ap-1 is highly homologous to osteopontin, it lacks a pentapeptide, YKQRA, that is present in the latter protein. There are a total of 43 encoded amino acid residues which differ between Ap-1 and osteopontin, out of which 28 are nonconservative substitutions. No immunological effector cell activity for osteopontin has been described. As a further distinction, osteopontin is reported to be present solely in bone (Franzen, A. and Heinegard, D., 1985, Biochem. J. 232:715-724; Oldberg, A., et al., 1986, Proc. Natl. Acad. Sci. U.S.A. 83:8819-8823).

A search of the PIR/NBRF protein sequence database for the KQR tripeptide present in Ap-1, revealed that the KQR tripeptide is uncommon; it is present in the data base in a frequency that is lower than that expected as estimated from the product of the individual frequencies of each amino acid. The KQR tripeptide is present within the glycosaminoglycan binding regions of RGD-containing proteins such as vitronectin (Suzuki, S., et al., 1985, EMBO J. 4:2519-2524), laminen, vitronectin (Jenne, D. and Stanley, K. K., 1985, EMBO J. 4:3153-3157), and human complement C4a. The presence of the KQR tripeptide and additional amino acid changes around the site of the KQR-containing pentapeptide in osteopontin generates a cluster of positive charges in a predicted alpha-helical configuration that has been pointed out as characteristic of binding sites for glycosaminoglycans (Lawler, J., 1981, Thromb. Res. 21:121-127; Jenne, D. and Stanley, K. K., 1985, EMBO J. 4:3153-3157; Suzuki, S., et al., 1985, EMBO J. 4:2519-2524).

In contrast, the Ap-1 KQR tripeptide does not appear to be within a glycosaminoglycan binding domain. One implication of this structural difference is that KQR-containing molecules within the RGD protein family may be limited to anatomical compartments containing a particular glycosaminoglycan. By contrast, Ap-1 activity may be independent of extracellular matrices. The experiments described herein indicate that the ability of soluble Ap-1 to form a gradient and to efficiently activate cells carrying receptors for the protein is not altered by the presence of extracellular matrices, such as collagen, gelatin, or gelatin/fibronectin complexes. Thus, Ap-1's activity may not be limited to particular tissues; it may attract and activate cells bearing Ap-1 receptors independent of the anatomical site of its production.

There is a marked increase in Ap-1 expression in lymphoid cells, particularly lymp nodes, from MRL-lpr/lpr, "lupus", mice. Overexpression of Ap-1 coincided with lymphoid hyperplasia and endogenous macrophage activation (FIG. 14), which also marks the onset of autoimmune disease (Theofilopoulos, A. N. and Dixon, F. J., 1985, Advances in Immunol. 37:269-392; Kelley, V. E. and Roths, J. B., 1985, Clin. Immunol. Immunop. 37:220-229; Kelley, V. E. and Roths, J. B., 1982, J. Immunol. 129(3):923-925). Since lymph nodes from these MRL-lpr/lpr mice contained 100-fold more lymphocytes than MRL +/+ age-matched controls, the total level of Ap-1 transcription after onset of MRL-lpr/lpr autoimmune disease is apparently extremely elevated. Possibly, the lpr gene acts in concert with an MRL associated gene to expand lymphoid cells which overproduce Ap-1.

In addition to production of Ap-1, which may account for abnormally high levels of activated macrophages, MRL/l mice contain T cells that produce high levels of a factor which enhances IgM and IgG secretion by B cells, called L-BCDF (Theofilopoulos, A. N. and Dixon, F. J., 1985, Advances in Immunol. 37:269-392. It is possible that Ap-1 induction of Ia+ macrophages may stimulate T cells to produce high levels of BCDF, as well as other factors (e.g., BSF-1) leading to increased production of immunoglobulin.

7. DEPOSIT OF MICROORGANISMS

The following cells carrying the listed plasmids have been deposited with the American Type Culture Collection, Rockville, Md., and have been assigned the listed accession numbers:

| Cell | Vector | Description | Accession Number |
|---|---|---|---|
| E. coli strain MC 1061 | pCD-Ap-1 (plasmid) | murine Ap-1 cDNA | 67615 |
| E. coli strain NM 538 | Hi92 (lambda phage derivative) | human genomic Ap-1 clone | 67616 |

The present invention is not to be limited in scope by the microorganisms deposited since the deposited embodiment is intended as a single illustration of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

What is claimed is:

1. An isolated DNA molecule comprising a nucleic acid sequence encoding a protein having the amino acid sequence as depicted in FIG. 2B.

2. An isolated DNA molecule comprising the nucleic acid sequence of FIG. 2B.

3. The DNA molecule of claim 1 which comprises a genomic DNA sequence.

4. The DNA molecule of claim 1 or 2 which comprises a cDNA sequence.

5. An isolated RNA molecule having a ribonucleic acid sequence complementary to the nucleic acid sequence of claim 1 or 2.

6. The DNA molecule of claim 1, in which the nucleic acid sequence is a mouse genomic sequence.

7. An isolated DNA molecule comprising a human genomic sequence hybridizable to the nucleic acid sequence of FIG. 2B, and which genomic sequence encodes a protein having the following properties:
   (i) immunological effector cell binding;
   (ii) immunological effector cell activation;
   (iii) immunological effector cell chemattraction;
   (iv) induction of immunological effector cell cytotoxicity; and
   (v) induction of granulocyte/monocyte progenitor cell differentiation.

8. A recombinant microorganism containing a vector comprising the DNA molecule of claim 1, 2, or 7.

9. The recombinant microorganism of claim 8 which is a bacterium.

10. The recombinant microorganism of claim 8 which is a yeast.

11. A recombinant nucleic acid vector comprising the DNA molecule of claim 1, 2, or 7.

12. A recombinant cell containing the nucleic acid vector of claim 11.

13. The recombinant cell of claim 12 which is mammalian.

14. The recombinant cell of claim 12 which is a bacterium.

15. The recombinant DNA vector pCD-Ap-1.

16. A recombinant cell containing the recombinant DNA vector of claim 15.

17. The recombinant cell of claim 16 which is mammalian.

18. The recombinant cell of claim 16 which is a bacterium.

19. The recombinant bacterium of claim 18 which is the Escherichia coli as deposited with the ATCC and assigned accession number 67615.

20. The recombinant DNA vector Hi92.

21. A recombinant bacterium containing the DNA vector of claim 20.

22. The recombinant bacterium of claim 21 which is the Escherichia coli, as deposited with the ATCC and assigned accession number 67616.

23. An isolated DNA molecule comprising the nucleic acid sequence as contained in the vector Hi92 in the recombinant bacterium deposited with the ATCC and assigned accession number 67616, encoding a protein characterized by at least one of the following properties:
 (i) immunological effector cell binding;
 (ii) immunological effector cell activation;
 (iii) immunological effector cell chemattraction;
 (iv) induction of immunnological effector cell cytotoxicity; and
 (v) induction of granulocyte/momocyte progenitor cell differentiation.

24. A recombinant microorganism containing a nucleic acid vector comprising the DNA molecule of claim 23.

25. The recombinant microorganism of claim 24 which is a bacterium.

* * * * *